(12) United States Patent
Black et al.

(10) Patent No.: US 7,211,561 B2
(45) Date of Patent: May 1, 2007

(54) METHOD FOR INDUCING SELECTIVE CELL DEATH OF MALIGNANT CELLS BY ACTIVATION OF CALCIUM-ACTIVATED POTASSIUM CHANNELS ($K_{CA}$)

(75) Inventors: Keith L. Black, Los Angeles, CA (US); Nagendra S. Ningaraj, Culver City, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 626 days.

(21) Appl. No.: 09/976,961

(22) Filed: Oct. 12, 2001

(65) Prior Publication Data

US 2003/0072748 A1    Apr. 17, 2003

(51) Int. Cl.
*A01N 33/02* (2006.01)
*A61K 31/13* (2006.01)

(52) U.S. Cl. .................. 514/12; 514/12; 514/663
(58) Field of Classification Search .............. 514/12, 514/45, 665, 663; 424/94.61
See application file for complete search history.

(56) References Cited

U.S. PATENT DOCUMENTS

| | | |
|---|---|---|
| 5,112,596 A | 5/1992 | Malfroy-Camine |
| 5,124,146 A | 6/1992 | Neuwelt |
| 5,215,985 A | 6/1993 | Murphy et al. |
| 5,256,688 A | 10/1993 | Grover et al. |
| 5,262,419 A | 11/1993 | Aberg et al. |
| 5,314,887 A | 5/1994 | Aldrich et al. |
| 5,399,587 A | 3/1995 | Garcia et al. |
| 5,416,097 A | 5/1995 | Erhardt et al. |
| 5,527,527 A | 6/1996 | Friden |
| 5,527,778 A | 6/1996 | Black |
| 5,578,599 A | 11/1996 | Diani et al. |
| 5,604,198 A | 2/1997 | Poduslo et al. |
| 5,670,477 A | 9/1997 | Poduslo et al. |
| 5,677,344 A | 10/1997 | Greenfield et al. |
| 5,679,706 A | 10/1997 | D'Alonzo et al. |
| 5,686,416 A | 11/1997 | Kozarich et al. |
| 5,693,627 A | 12/1997 | Schieven |
| 5,695,751 A | 12/1997 | Friedman et al. |
| 5,760,230 A | 6/1998 | Schohe-Loop et al. |
| 5,869,509 A | 2/1999 | Romine et al. |
| 5,877,210 A | 3/1999 | Schieven |
| 5,922,735 A | 7/1999 | Sit et al. |
| 2003/0036199 A1* | 2/2003 | Bamdad et al. ............. 435/975 |

FOREIGN PATENT DOCUMENTS

| | | |
|---|---|---|
| EP | 0 351 767 A2 | 1/1990 |
| EP | 0 555 681 A1 | 8/1993 |
| EP | 0 575 749 A2 | 12/1993 |
| WO | WO 91/16355 | 10/1991 |
| WO | WO 97/18332 A1 | 5/1997 |
| WO | WO 97/31654 | 9/1997 |
| WO | WO 00/23102 | 4/2000 |

OTHER PUBLICATIONS

Gulbins et al. (Proc. Natl. Acad. Sci. USA 1997, 94: 7661-7666).*
Nietsch et al. (J. Biol. Chem. 2000, 275 (27): 20556-20561).*
Lauritzen et al. (J. Neurochem. 1997, 69: 1570-1579).*
Choi et al. (Cancer Letters 1999, 147: 85-93).*
Kim et al. (Pharmacology 2000, 60 (2): 74-81).*
Wang et al. (Am. J. Physiol. Heart Cir. Physiol. 2004; 287: H2070-H2077.*
Yamada et al. (Cancer Research 1987; 47: 2123-2128.*
Adeagbo, A. S., 1-Ethyl-2-benzimidazolinone stimulates endothelial K (Ca) channels and nitric oxide formation in rat mesenteric vessels, *Eur J. Pharmacol*, 379(2-3):151-9 (Aug. 27, 1999). Abstract Only.
Akar, F. et al, Protective effect of cromakalim and diazoxide, and proulcerogenic effect of glibenclamide on indomethacin-induced gastric injury, *Eur J. Pharmacol*, 374(3):461-70 (Jun. 25, 1999). Abstract Only.
Andrade, S.P. et al., Pharmacological reactivity of neoplastic and non-neoplastic associated neovasculature to vasoconstrictors, *Int J Exp Pathol*, 79(6):425-32 (Dec. 1998). Abstract Only.
Armstead. W.M., Contribution of kca channel activation to hypoxic cerebrovasodilatation does not involve NO, *Brain Res*. 799(1):44-8 (Jul. 13, 1998). Abstract Only.
Bang, L. et al., Nitroglycerin-mediated vasorelaxation is modulated by endothelial calcium-activated potassium channels, *Cardiovasc Res*, 43(3):772-8 (Aug. 15, 1999). Abstract Only.
Becker, E.M. et al., The vasodilator-stimulated phosphoprotein (VASP):target of YC-1 and nitric oxide effects in human and rat platelets, *J. Cardiovasc Pharmacol*, 35(3):390-7 (Mar. 2000). Abstract Only.
Black, K.L. et al., Selective opening of the blood-tumor barrier by intracarotid infusion of leukotriene $C_4$, *J. Neurosurg*, 72:912-916 (Jun. 1990).
Bowman, T. et al., STATs in oncogenesis, *Oncogene*, 19(21):2474-88 (May 15, 2000). Abstract Only.

(Continued)

*Primary Examiner*—Jeffrey Siew
*Assistant Examiner*—Brandon Fetterolf
(74) *Attorney, Agent, or Firm*—Seth D. Levy; Davis Wright Tremaine LLP

(57) ABSTRACT

Disclosed are a method of inducing apoptosis of a malignant cell, which employs a calcium-activated potassium channel ($K_{Ca}$) activator and is useful for treating a malignant tumor in a human subject. Also disclosed are methods of selectively inhibiting the proliferation of malignant cells compared to non-malignant cells in a mixed population of malignant and non-malignant cells and of inhibiting the growth of a malignant tumor, such as a glial tumor, in a mammalian subject. A kit for inducing apoptosis of malignant cells is also disclosed.

18 Claims, 20 Drawing Sheets

OTHER PUBLICATIONS

Brian, J.E., Jr. et al., Recent insights into the regulation of cerebral circulation, *Clin Exp Pharmacol Physiol*, 23(6-7):449-57 (Jun.-Jul. 1996). Abstract Only.

Brismar, T. et al., Mechanism of high K+ and Ti+ uptake in cultured human glioma cells, *Cell Mol Neurobiol*. 15(3):351-60 (Jun. 1995). Abstract Only.

Brismar, T. et al., Thallium-201 uptake relates to membrane potential and potassium permeability in human glioma cells, *Brain Res*, 500(1-2):30-6 (Oct. 23, 1989). Abstract Only.

Burg, M.A. et al., NG2 proteoglycan-binding peptides target tumor neovasculature, *Cancer Res*, 59(12):2869-74 (Jun. 15, 1999). Abstract Only.

Burrows, F.J. et al., Eradication of large solid tumors in mice with an immunotoxin directed against tumor vasculature, *Proc Natl Acad Sci U S A*, 90(19):8996-9000 (Oct. 1, 1993). Abstract Only.

Butt, A.M., Effect of histamine and antagonists on electrical resistance across the blood-brain barrier in rat brain-surface microvessels, *Brain Res*, 569(1):100-5 (Jan. 8, 1992). Abstract Only.

Butt, A.M., Effect of inflammatory agents on electrical resistance across the blood-brain barrier in pial microvessels of anaesthetized rats, *Brain Res*, 696(1-2):145-50 (Oct. 23, 1995). Abstract Only.

Butt, E. et al., Inhibition of cyclic GMP-dependent protein kinase-mediated effects by (Rp)-8-bromo-PET-cyclic GMPS, *Br J. Pharmacol*, 116(8):3110-6 (Dec. 1995). Abstract Only.

Bychkov, R. et al., Calcium-activated potassium channels and nitrate-induced vasodilation in human coronary arteries, *J. Pharmacol Exp Ther*, 285(1):293-8 (Apr. 1998). Abstract Only.

Cai, S. et al., Single-channel characterizationof the pharmacological properties of the K(Ca2+) channel of intermediate conductance in bovine aortic endothelial cells, *J Membr Biol*, 163(2):147-58 (May 15, 1998). Abstract Only.

Chang, S.S. et al., Five different anti-prostate-specific membrane antigen (PSMA0 antibodies confirm PSMA expression in tumor-associated neovasculature, *Cancer Res*, 59(13):3192-8 (Jul. 1, 1999). Abstract Only.

Chaplin, D.J. et al., Anti-vascular approaches to solid tumour therapy: evaluationof combretastatin A4 phosphate, *Anticancer Res*. 19(1A):189-95 (Jan.-Feb. 1999). Abstract Only.

Chassande. O. et al., The Na+/K+/Cl- cotransport in C6 glioma cells. Properties and role in volume regulation, *Eur J. Biochem*, 171(3):425-33 (Feb. 1, 1988). Abstract Only.

Chess-Williams, R. et al., In vitro investigationof the bladder-vascular selectivity of levcromakalim and YM934 in human tissues, *BJU Int*, B3(9):1050-4 (Jun. 1999). Abstract Only.

Chen, C.H. et al., Ntric oxide activates Ca2+-activated K+ channels in cultured bovine adrenal chromaffin cells, *Neurosci Lett*, 248(2):127-9 (May 29, 1998). Abstract Only.

Dark. G.G. et al., Combretastatin A-4, an agent that displays potent and selective toxicity toward tumor vasculature, *Cancer Res*, 57 (10):1829-34 (May 15, 1997). Abstract Only.

Denekamp, J. et al., Vasculature and microenvironmental gradients: the missing links in novel approaches to cancer therapy? *Adv Enzyme Regul*, 38:281-99 (1998). Abstract Only.

Desai, S.B. et al., Tumor angiogenesis and endothelial cell modulatory factors, *J. Immunother*, 22(3):186-211 (May 1999). Abstract Only.

D'hahan, N. et al., A transmembrane domain of the sulfonylurea receptor mediates activation of ATP-sensitive K(+) channels by K(+) channel openers, *Mol Pharmacol*. 56(2):308-15 (Aug. 1999). Abstract Only.

Duda, T. et al., Mutations in the Rod Outer Segment Membrane Guanylate Cyclase in a Cone-Rod Dystrophy Cause Defects in Calcium Signaling, *Biochemistry*, 38(42):132912-13919 (Oct. 19, 1999), Abstract Only.

Faraci, F.M. et al., Responses of cerebral arterioles to N-methyl-D-aspartate and activation of ATP-sensitive potassium channels in old rats, *Brain Res*, 654(2):349-51 (Aug. 22, 1994). Abstract Only.

Faraci, F.M. et al., Potassium channels and the cerebral circulation, *Clin Exp Pharmacol Physiol*, 23(12):1091-5 (Dec. 1996). Abstract Only.

Feelisch, Martin, The use of nitric oxide donors in pharmacological studies, *Naunyn-Schmiedeberg's Arch Pharmacol*, 358:113-122 (Springer-Veriag 1998).

Ferrero, R. et al., Comparative effects of several nitric oxide donors on intracellular cyclic GMP levels in bovine chromaffin cells: correlation with nitric oxide production, *Br J. Pharmacol*. 127(3):779-87 (Jun. 1999). Abstract Only.

Friebe, A. et al., Mechanism of YC-1-induced activation of soluble guanylyl cyclase, *Mol Pharmacol*, 53(1):123-7 (Jan. 1998). Abstract Only.

Fukao, M. et al., Cyclic GMP-dependent protein kinase activates cloned BKCa channels expressed in mammalian cells by direct phosphorylationat serine 1072, *J Biol Chem*, 274(16): 10927-35 (Apr. 16, 1999). Abstract Only.

Fukamura, D. et al., Role of nitric oxide in angiogenesis and microcirculation in tumors, *Cancer and Metastasis Reviews*, 17:77-89 (1998).

Fullerton, D.A. et al., Effective control of pulmonary vascular resistance with inhaled nitric oxide after cardiac operation, *J. Thorac Cardiovasc Surg*, 111(4):753-62; discussion 762-3 (Apr. 1996). Abstract Only.

Gbadegesin, M. et al., Hypoxia modulates nitric oxide-induced regulation of NMDA receptor currents and neuronal cell death, *Am J Physiol*, 277 (4 Pt 1):C673-83 (Oct. 1999). Abstract only.

Goldstein, G.W. et al., In vitro studies of the blood-brain barrier using isolated brain capillaries and cultured endothelial cells, *Ann N Y Acad Sci*, 481:202-13 (1986). Abstract Only.

Goto, K. et al., Sympathetic control of arterial membrane potential by ATP-sensitive K(+)-channels, *Hypertension*, 35 (1 Pt 2):379-84 (Jan. 2000) Abstract Only.

Gulbins, E. et al., Ceramide-induced inhibition of T lymphocyte voltage-gated potassium channel is mediated by tyrosine kinases, *Proc natl Acad Sci M S A*, 94(14):7661-6 (Jul. 8, 1997). Abstract Only.

Hardy, P. et al., A major role for prostacyclin in nitric oxide-iinduced ocular vasorelaxation in the piglet, *Circ Res*, 83(7):721-9 (Oct. 5, 1998). Abstract Only.

Harland, S.P. et al., Expressionof endothelin(A) receptors in human gliomas and meningiomas, with high affinity for the selective antagonist PC156707, *Neurosurgery*, 43(4):890-8; discussion 898-9, (Oct. 1998) Abstract Only.

He, P. et al., cGMP modulates basal and activated microvessel permeability independently of (Ca2+)i, *Am J Physiol*, 274(6 Pt 2):H1865-74 (Jun. 1998). Abstract Only.

Herrera, G.M. et al., Maintained vasodilatory response to cromakalim after inhibition of nitric oxide synthesis, *J Cardiovasc Pharmacol*, 31(6):921-9 (Jun. 1998). Abstract Only.

Holland, M. et al., Effects of the BKCa channel activator, NS1619, on rat cerebral artery smooth muscle, *Br J Pharmacol*, 117(1):119-29 (Jan. 1996). Abstract Only.

Holschermann, H. et al., Dual Role of cGMP in modulation of macromolecule permeability of aortic endothelial cells, *Am J Physiol*, 272(1 Pl 2):H91-8 (Jan. 1997), Abstract Only.

Islam, T.C. et al., BTK mediated apoptosis, a possible mechanism for failure to generate high titer retroviral producer clones, *J Gene Med*, 2(3):204-9 (May-Jun. 2000). Abstract Only.

Jackson, W.F. et al., Prostacyclin-induced vasodilation in rabbit heart is mediated by ATP-sensitive potassium channels, *Am J Physiol*, 264(1 Pt 2):H238-43 (Jan. 1993). Abstract Only.

Jain, R.K., Vascular and interstitial barriers to delivery of therapeutic agents in tumors, *Cancer Metastasis Rev*, 9(3):253-66 (Nov. 1990). Abstract Only.

Keep, R.F. et al., Potassium transport at the blood-brain and blood-CSF barriers, *Adv Exp Med Biol*, 331:43-54 (1993). Abstract Only.

Kiegler-Jensen, N. et al., Inhaled nitric oxide in the evaluation of heart transplant candidates with elevated pulmonary vascular resistance, *J Heart Lung Transplant*, 13(3):366-75 (May-Jun. 1994). Abstract Only.

Kim, J. A. et al., Ca2+ influx mediates apoptosis induced by 4-aminopyridine, a K+ channel blocker, in HepG2 human hepatoblastoma cells, *Pharmacology*, 60(2):74-81 (Feb. 2000). Abstract Only.

Kimura, M. et al., Responses of human basilar and other isolated arteries to novel nitric oxide donors, *J Cardiovasc Pharmacol*, 32(5):695-701 (Nov. 1998). Abstract Only.

Kinoshita, H. et al., Differential effects of lidocaine and mexiletine on relaxations to ATP-sensitive K+ channels openers in rat aortas. *Anesthesiology*, 90(4): 1165-70 (Apr. 1999). Abstract Only.

Kitazono, T. et al., Role of potassium channels in cerebral blood vessels, *Stroke*, 26(9):1713-23 (Sep. 1995). Abstract Only.

Koesling, D., Modulators of soluble guanylyl cyclase, *Naunyn-Schmiedeberg's Arch Pharmacol*, 358:123-126 (Springer-Veriag1998).

Kurtz, A. et al., Mode of nitric oxide action on the renal vasculature, *Acta Physiol Scand*, 168(1):41-45 (Jan. 2000). Abstract Only.

Lauritzen, I. et al., The potassium channel opener (-)-cromakalim prevents glutamate-induced cell death in hippocampal neurons, *J Neurochem*, 69(4):1570-9 (Oct. 1997). Abstract Only.

Lee, Y.S. et al., In vitro antitumor activity of cromakalim in human brain tumor cells, *Pharmacology*, 49(2):69-74 (Aug. 1994). Abstract Only.

Liu, Q. et al., Hypoxic dilatation of porcine small coronary arteries: role of endothelium and KATP-channels, *Br J Pharmacol*, 120(4):728-34 (Feb. 1997). Abstract Only.

Liu, S.M. et al., Nitric acid and cGMP regulate endothelial permeability and F-actin distributinin hydrogen peroxide-treated endothelial cells. *Exp Cell Res*, 235(1):238-44 (Aug. 25, 1997). Abstract Only.

Lohse, M., Pharamcology of NO:cGMP signal transduction, *Naunyn-Schmiedeberg's Arch Pharmacol*, 538:111-112(Springer-Veriag 1998). Abstract Only.

Malayev, A.A. et al., Mechanism of clofilium block of the human Kv1.5 delayed rectifier potassium channel, *Mol Pharmacol*, 47(1):198-205 (Jan. 1995). Abstract Only.

Manor, D. et al., Interactions among calcium compartments in C6 rat glioma cells:involvement of potassium channels, *J Physiol (Lond)*, 478 (Pt 2):251-63 (Jul. 15, 1994). Abstract Only.

Matsukado, K. et al., Selective increase in blood-tumor barrier permeability by calcium antagonists in transplanted rat brain tumors, *Acta Neurochir Suppl (Wien)*, 60:403-5 (1994). Abstract Only.

Mayer, Bernd et al.., Nitric oxide synthases: catalytic function and progress towards selective inhibition, *Naunyn-Schmiedeberg's Arch Pharmacol*, 358:127-133 (Springer-Veriag 1998).

Miller, T.R. et al., Pharmacological and molecular characterization of ATP-sensitive K+ channels in the TE671 human medulloblastoma cell line, *Eur J Pharmacol*, 370(2):179-85 (Apr. 9, 1999). Abstract Only.

Miyaji, Katsuya et al., Effect of tyrphostin on cell growth and tyrosine kinase activity of epidermal growth factor receptor in human gliomas, *J Neurosurg*, 81:411-419 (1994).

Molema, G. et al., Tumor vascular endothelium: barrier or target in tumor directed drug delivery and immunotherapy, *Pharm Res*, 14(1):2-10 (Jan. 1997). Abstract Only.

Nadeau, H. et al., ROMK1 (Kir1.1) causes apoptosis and chronic silencing of hippocampal neurons, *J Neurophysiol*, 84(2):1062-75 (Aug. 2000). Abstract Only.

Nietsch, Hubert H. et al., Activation of Potassium and Chloride Channels by Tumor Necrosis Factor a, *Journal of Biological Chemistry*, 275(27):20556-20561 (Jul. 7, 2000).

Ningaraj, N: S. et al., Nitric Oxide Donors Increase Blood Brain Tumor Barrier Permeability Via $K_{CA}$ Channels, *Blood Brain Barrier: Models and Mechanisms*, Sunday PM, #126.8, Society for Neuroscience, 30th Annual Meeting, New Orleans, LA, 26 Part 1 (Nov. 4-9, 2000). Abstract Only.

Ningaraj, Nagendra S. et al., Tumor, Role of ATP-sensitive K+ Channels in Blood-Brain Tumor Barrier Permeability, Congress of Neurological Surgeons Annual Meeting, 50th Anniversary Celebration, Poster Program Book, Abstract # 430, (Sep. 23-28, 2000).

Ningaraj, Nagendra S. et al., Tumor, Ca2+-dependent K+ Channels Are a Key Regulator of Blood-Brain Tumor Barrier Permeability, Congress of Neurological Surgeons Annual Meeting, 50th Anniversary Celebration, Poster Program Book, Abstract # 438, (Sep. 23-28, 2000).

Nogami, K. et al., Role of Factor VIII C2 Domain in Factor VIII Binding to Factor Xa, *J Biol. Chem*, 274(43):31000-31007 (Oct. 22, 1999). Abstract Only.

O'Donnell, M.E. et al., Cerebral microvascular endothelial cell Na-K-Cl cotransport: regulation by astrocyte-conditioned medium, *Am J Physiol*, 268(3 Pt 1):C747-54 (Mar. 1995). Abstract Only.

Ohizumi, I. et al., Antibody-based therapy targeting tumor vascular endothelial cells suppresses solid tumor growth in rats, *Biochem Biophys Res Commun*, 236(2):493-6 (Jul. 18, 1997). Abstract Only.

Ohta, Y. et al., Tumor angiogenesis and recurrence in stage 1 non-small cell lung cancer, *Ann Thorac Surg*, 68(3):1034-8 (Sep. 1999). Abstract Only.

Panchal, R.G., Novel therapeutic strategies to selectively kill cancer cells, *Biochem Pharmacol*, 55(3):247-52 (Feb. 1, 1998). Abstract Only.

Smoak, I.W., Cromakalim: embryonic effects and reduction of tolbutamide-induced dysmorphogenesis in vitro, *Teratology*, 60(5):260-264 (Nov. 1999). Abstract Only.

Smolenski, A. et al., Functional analysis of cGMP-dependent protein kinases I and II as mediators of NO/cGMP effects, *Naunyn-Schmiedenberg's Arch Pharmacol*, 358:134-138 (Springer-Veriag 1988).

Solina, A. et al., A comparison of inhaled nitric oxide and milrinone for the treatment of pulmonary hypertension in adult cardiac surgery patients, *J Cardiothorac Vasc Anesth* 14(1):12-7 (Feb. 2000). Abstract Only.

Sugai, K. et al., Levcromakalim decreases cytoplasmic Ca2+ and vascular tone in basilar artery of SAH model dogs, *J Cardiovasc Pharmacol*, 33(6):868-75 (Jun. 1999). Abstract Only.

Teramoto, N. et al., Comparative studies on the relaxing action of several adenosine 5'-triphosphate-sensitive K+ channel openers in pig urethra, *J Smooth Muscle Res*, 35(1):11-22 (Feb. 1999). Abstract Only.

Thorpe, P.E. et al., Antibody-directed targeting of the vasculature of solid tumors, *Breast Cancer Res Treat*, 36(2):237-51 (1995). Abstract Only.

Toyoda, K. et al., Role of ATP-sensitive potassium channels in brain stem circulation during hypotension, *Am J Physiol*, 273(3 Pt 2):H1342-6 (Sep. 1997). Abstract Only.

Uchida, Mikito et al., Cyclic GMP-dependent Blood-Brain Tumor Barrier Permeability is Not Mediated by Cyclic GMP-Dependent Protein Kinase, Congress of Neurological Surgeons Annual Meeting, 50th Anniversary Celebration, Poster Program Book, #440 (Sep. 23-28, 2000).

Vaali, K et al., Relaxing effects of NO donors on guinea pig trachea in vitro are mediated by calcium-sensitive potassium channels, *J Pharmacol Exp Ther*, 286(1):110-4 (Jul. 1998). Abstract Only.

van Hinsbergh, V. W. et al., Angiogenesis and anti-angiogenesis: perspectives for the treatment of solid tumors, *Ann Oncol*, 10 Suppl 4:60-3 (1999) Abstract Only.

Vodovotz, Y et al., Regulation of transforming growth factor beta1 by nitric oxide, *Cancer Res*, 59(9):2142-9 (May 1, 1999) Abstract Only.

Walter, J. J. et al, Angiostatin binds to smooth muscle cells in the coronary artery and inhibits smooth muscle cell proliferation and migration in vitro, *Arterioscler Thromb Vasc Biol*, 19(9):2041-8 (Sep. 1999). Abstract Only.

Wickenden, A. D. et al., Comparison of the effects of the K(+)-channel openers cromakalim and minoxidil sulphate on vascular smooth muscle, *Br J Pharmacol*, 103(1):1148-52 (May 1991). Abstract Only.

Wulff, Heike et al., Design of a potent and selective inhibitor of the intermediate-conductance $Ca^{2+}$-activated $K^+$ channel, IKCa1: A potential immunosuppressant, *PNAS*, 97(14):8151-8156 (Jul. 5, 2000).

Yakubu, M. A. et al., Hematoma-induced enhanced cerebral vasoconstrictions to leukotriene C4 and endothelin-1 in piglets: role of prostanoids, *Pediatr Res*, 38(1):119-23 (Jul. 1995). Abstract Only.

Web site: Sigma-Aldrich, Search Results, p. 1; http://vsearch.sial.com/search97cgi/s97_cgi, downloaded May 31, 2000.

Web site: NO Donors/Precursors, TOCRIS, pp. 1-2; http://www.tocris.com/cat/nodonorstxt.html, downloaded May 31, 2000.

Patel, A.I. et al., Activation of guanosine 3',5'-cyclic monophosphate (cGMP)-dependent protein kinase in rabbit aorta by nitroglycerin and sodium nitroprusside, *J Pharmacol Exp Ther*, 283(2):885-93 (Nov. 1997).

Patel, A.I. et al., Activation of guanosine 3',5'-cyclic monophosphate (cGMP)-dependent protein kinase in rat vas deferens and distal colon is not accompanied by inhibition of contraction, *J Pharmacol Exp Ther*, 283(2):894-900 (Nov. 1997). Abstract Only.

Patel, H.J. et al., Inhibition of cholinergic neurotransmission in guinea pig trachea by NS1619, a putative activator of large-conductance, calcium-activated potassium channels, *J Pharmacol Exp Ther*, 286(2):952-8 (Aug. 1998). Abstract Only.

Rajek, A. et al., Inhaled nitric oxide reduces pulmonary vascular resistance more than prostaglandin E(1) during heart transplantation, *Anesth Analg*, 90(3):523-30 (Mar. 2000). Abstract Only.

Ran, S. et al., Infarction of solid Hodgkin's tumors in mice by antibody-directed targeting of tissue factor to tumor vasculature, *Cancer Res*, 58(20):4646-53 (Oct. 15, 1998). Abstract Only.

Reddy, E.P. et al., IL-3 signaling and the role of Src kinases, JAKs and STATs: a covert liaison unveiled, *Oncogene*, 19(21):2532-47 (May 15, 2000). Abstract Only.

Redrobe, J.P. et al., The effect of the potassium channel activator, cromakalim, on antidepressant drugs in the forced swimming test in mice, *Fundam Clin Pharmacol*, 10(6):524-8 (1996). Abstract Only.

Rettig, W.J. et al., Identification of endosialin, a cell surface glycoprotein of vascular endothelial cells in human cancer, *Proc Natl Acad Sci U S A*, 89(22):10832-6 (Nov. 15, 1992). Abstract Only.

Revest, P.A. et al., The transendothelial DC potential of rat blood-brain barrier vessels in situ, *Adv Exp Med Biol*, 331:71-4 (1993). Abstract Only.

Revest, P.A. et al., Transendothelial electrical potential across pial vessels in anaesthetised rats: a study of ion permeability and transport at the blood-brain barrier, *Brain Res*, 652(1):76-82 (Jul. 25, 1994). Abstract Only.

Robertson, Blair E. et al., cGMP-dependent protein kinase activates Ca-activated K channels in cerebral artery smooth muscle cells, *Am. J. Physiol.*, vol. 265, pp. C299-C303 (1993).

Salom, J.B. et al., Relaxant effects of sodium nitroprusside and NONOates in rabbit basilar artery, *Pharmacology*, 57(2):79-87 (Aug. 1998). Abstract Only.

Salom, J.B. et al., Comparative relaxant effects of the NO donors sodium nitroprusside, DEA/NO and SPER/NO in rabbit carotid arteries, *Gen Pharmacol*, 32(1):75-9 (Jan. 1999). Abstract Only.

Salom, J.B. et a;/, Relaxant effects of sodium nitroprusside and NONOates in goat middle cerebral artery: delayed impairment by global ischemia-reperfusion, *Nitric Oxide*, 3(1):85-93 (1999). Abstract Only.

Sandstrom, P.E. et al., Identification of potassium flux pathways and their role in the cytotoxicity of estramustine in human malignant glioma, prostatic carcinoma and pulmonary carcinoma cell lines, *Eur J Cancer*, 30A(12):1822-6 (1994). Abstract Only.

Schilling, L. et al., Opening of the blood-brain barrier during cortical superfusion with histamine, *Brain Res*, 653(1-2):298-96 (Aug. 8, 1994). Abstract Only.

Serfass, L. et al., Effect of heme oxygenase inhibitors on soluble guanylyl cyclase activity, *Arch Biochem Biophys*, 359(1):8-16 (Nov. 1, 1998). Abstract Only.

Sobey, C.G. et al., Mechanisms of bradykinin-induced cerebral vasodilatation in rats. Evidence that reactive oxygen species activate K+ channels, *Stroke*, 28(11):2290-4; discussion 2295 (Nov. 1997). Abstract Only.

Sobey, C.G. et al., Inhibitory effect of 4-aminopyridine on responses of the basilar artery to nitric oxide, *Br J Pharmacol*, 126(6): 1437-43 (Mar. 1999). Abstract Only.

XP-002195899—Oak. Z. et al., Effects of Cyclic GMP on Microvascular Permeability of the Cerebral Cortex, *Microvascular Research*. vol. 58, pp. 35-40 (1999).

XP-002195900—Role of nitric oxide in histamine-induced increases in permeability of the blood-brain barrier. (Mayhan. William G., *Brain Research*. vol. 743. pp70-76 (1996).

XP-002195901—Bartus. R. T. et al., Controlled Modulation of BBB Permeability Using the Bradykinin Agonist, RMP-07. *Experimental Neurology*. vol. 142. pp. 14-28 (1996).

\* cited by examiner

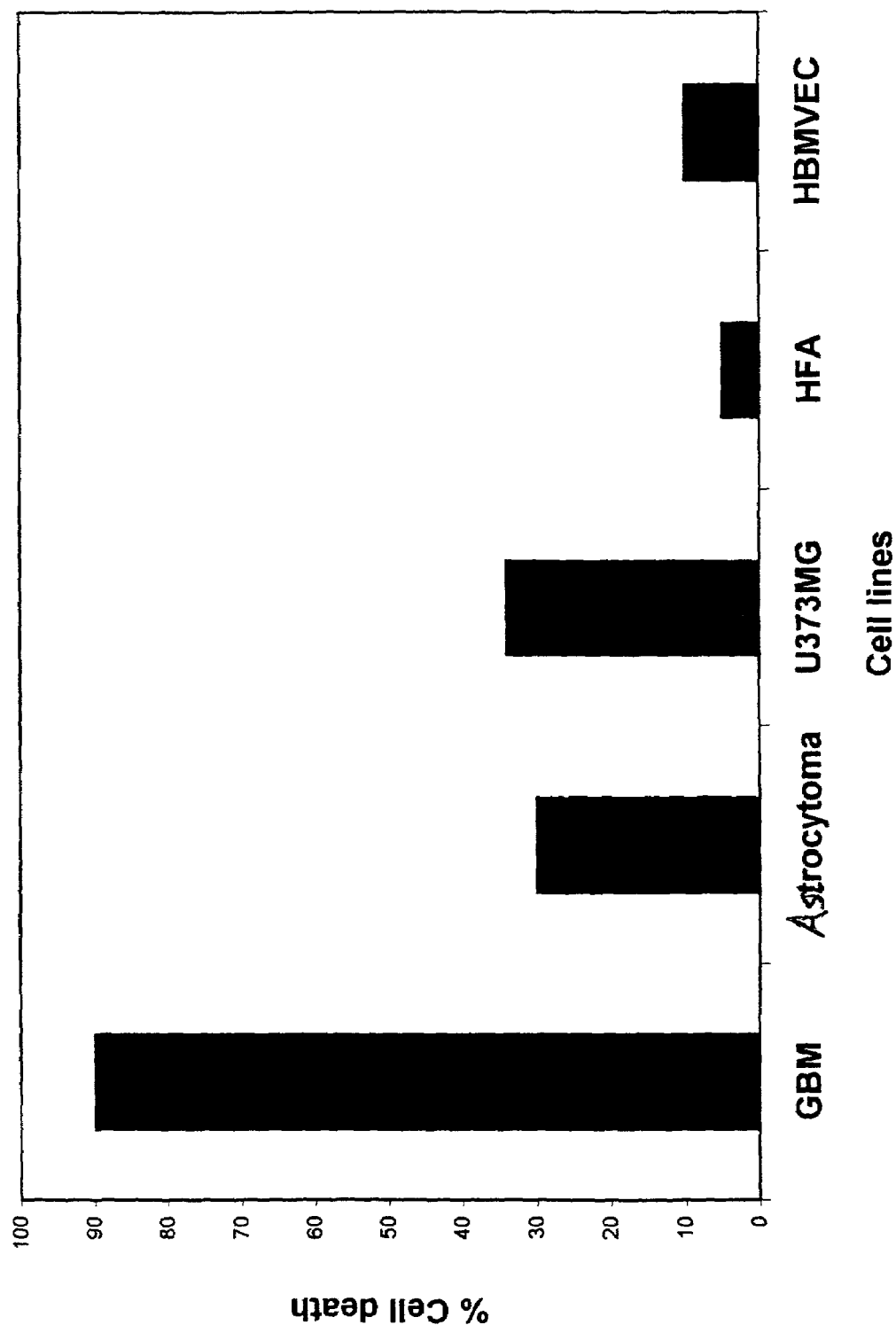

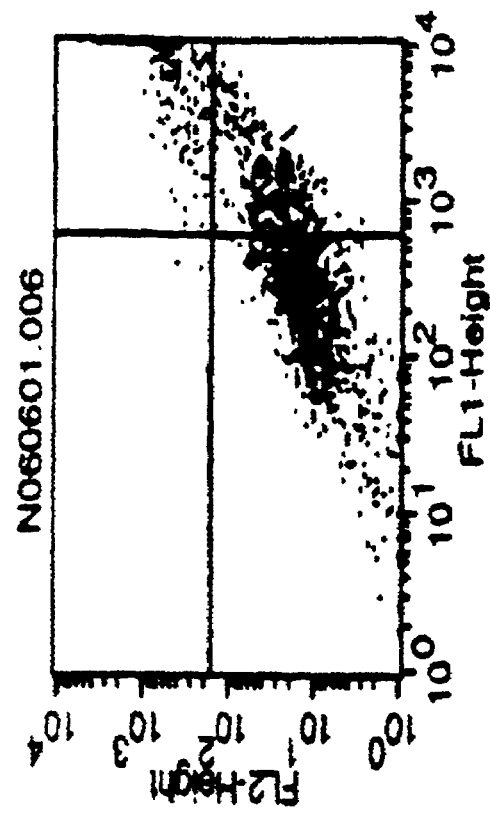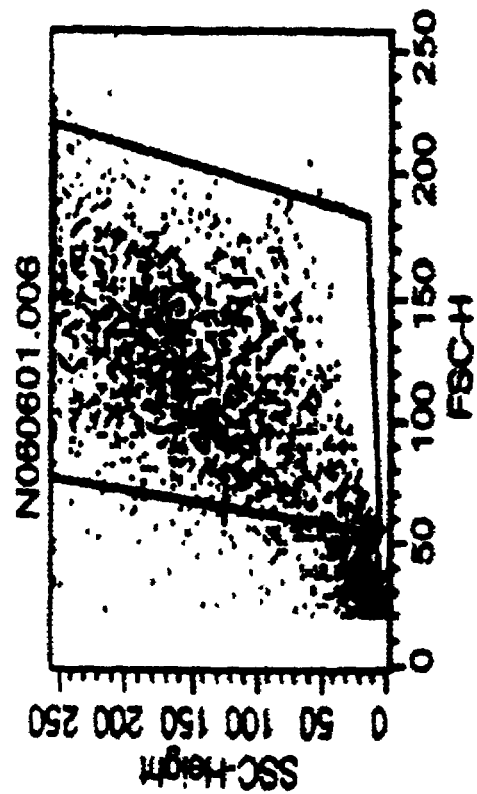
Figure 5B

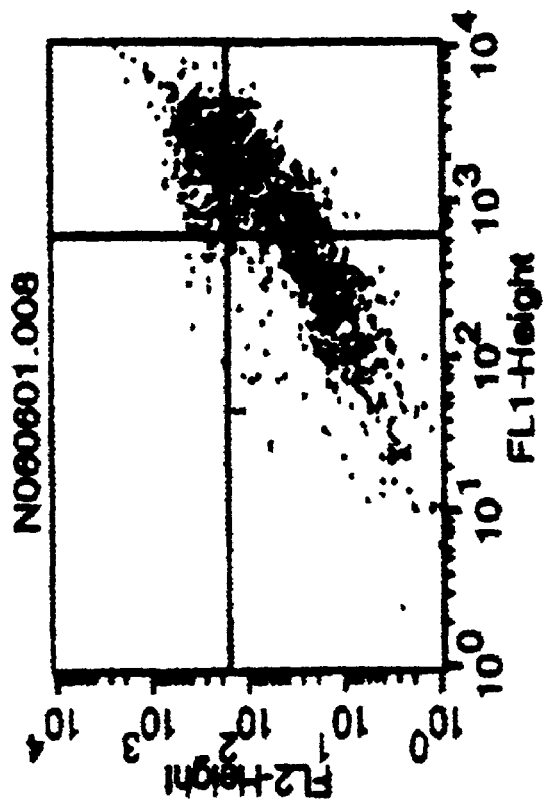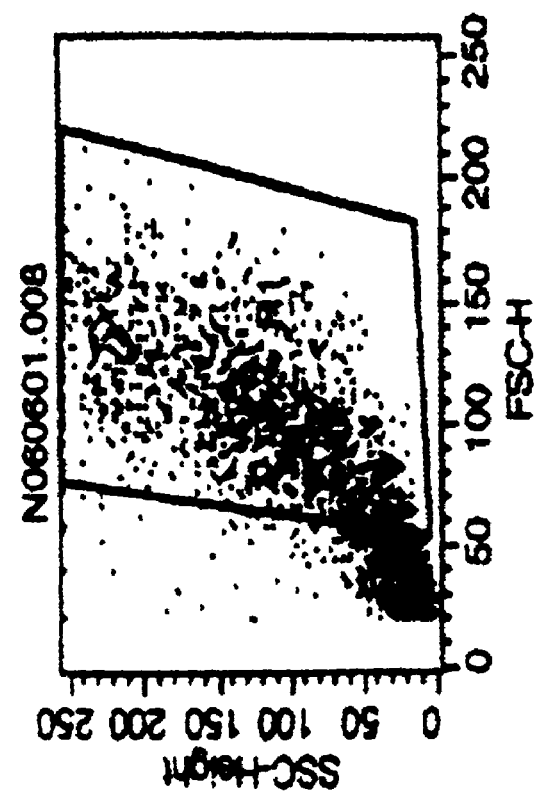
Figure 5C

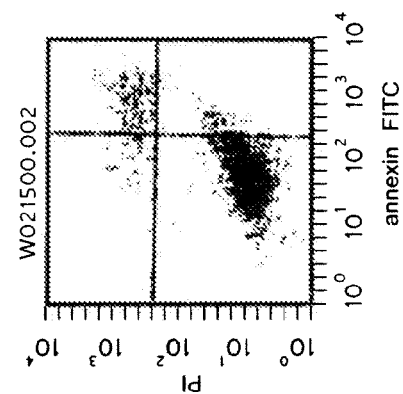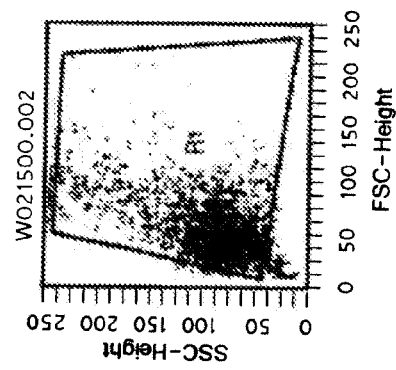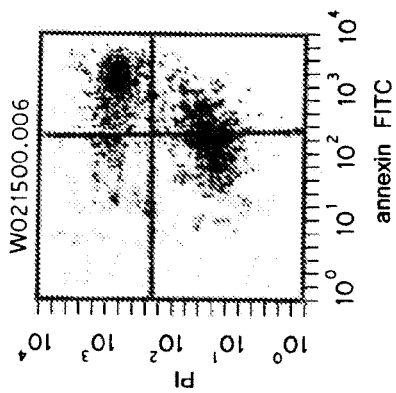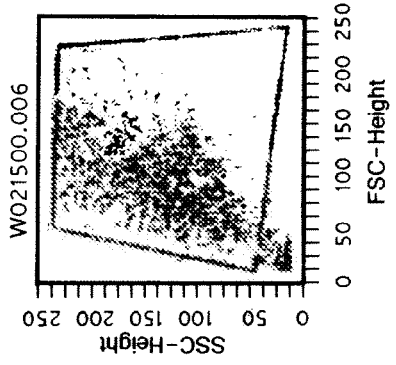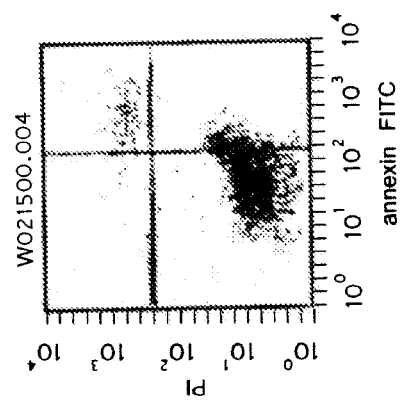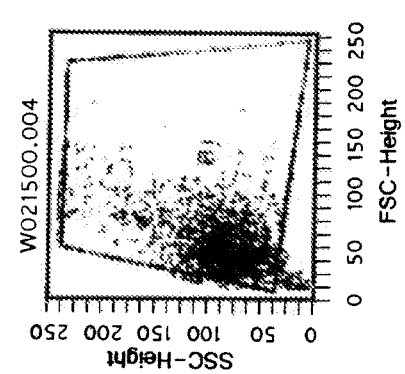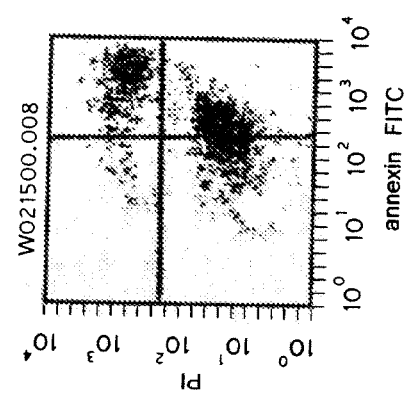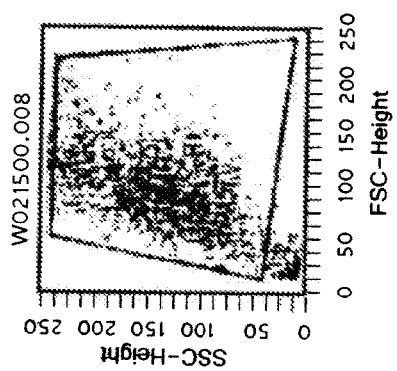
Figure 6C
Figure 6D
Figure 6E
Figure 6F

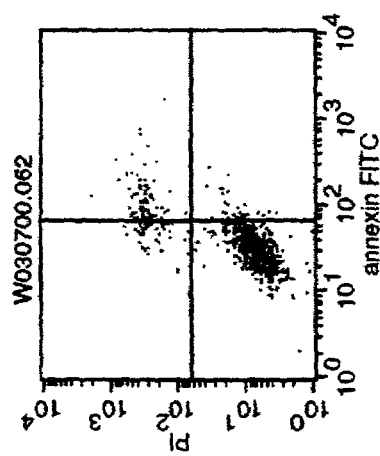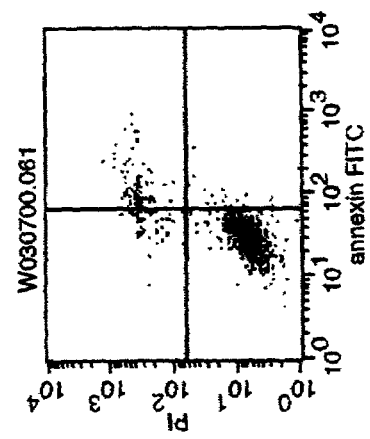
Figure 7C
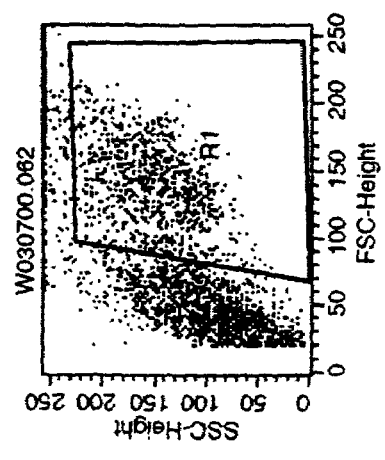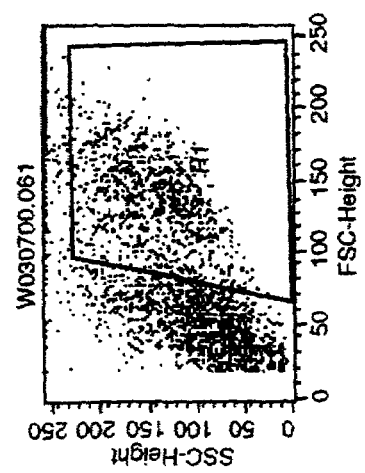
Figure 7D

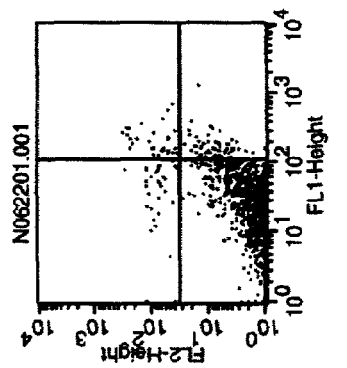
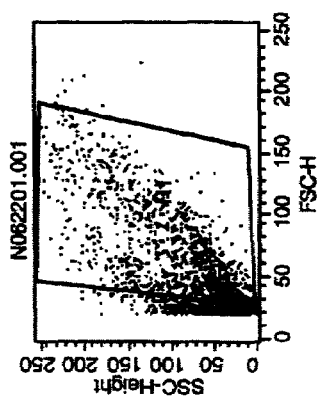
Figure 8B
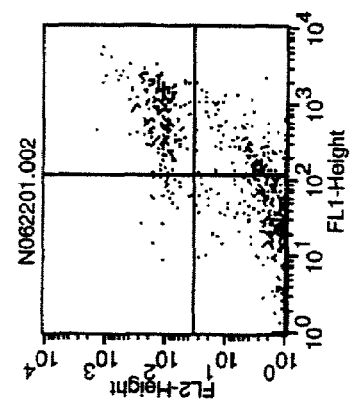
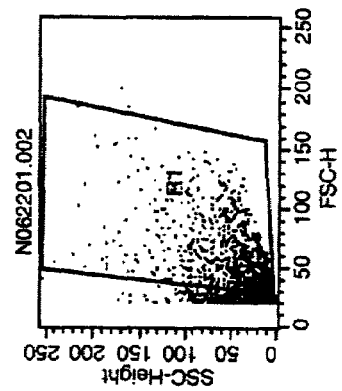
Figure 8A

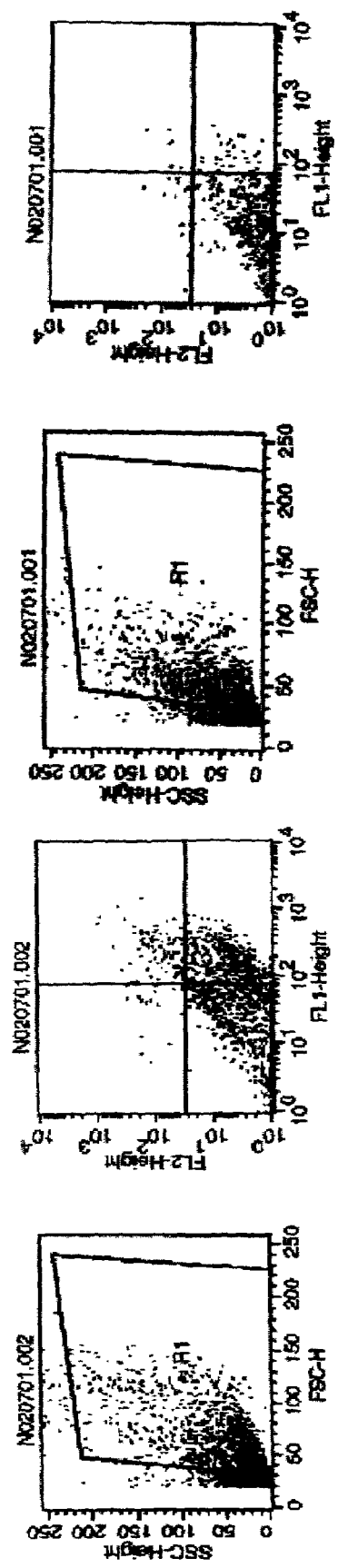
Figure 8H
Figure 8G
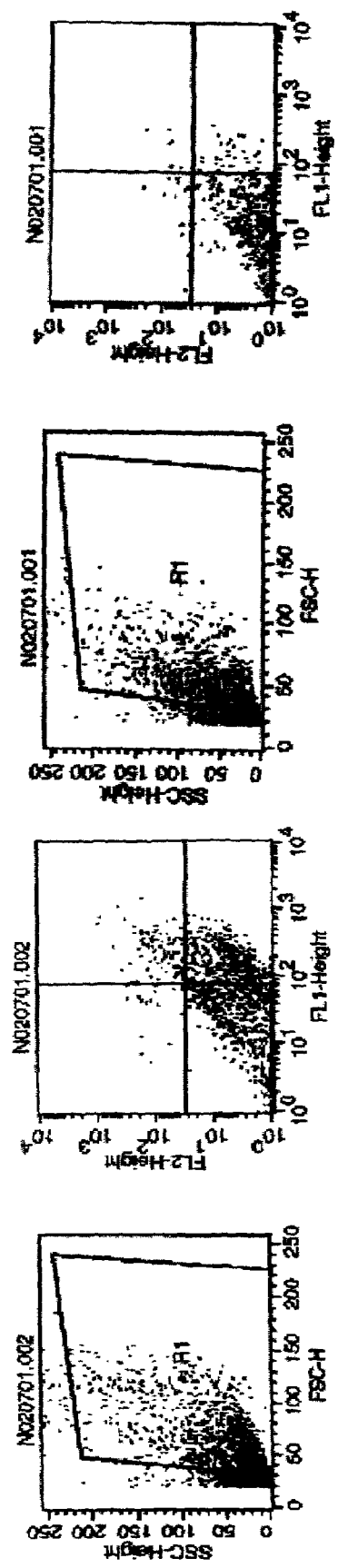

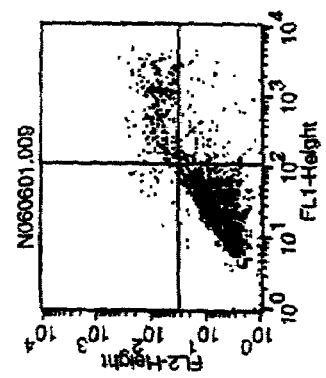
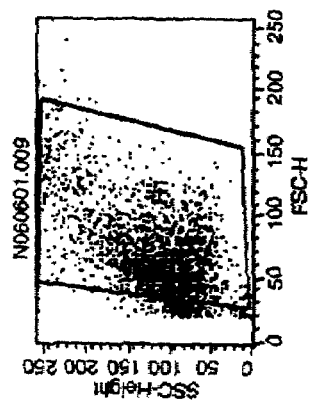
Figure 8J
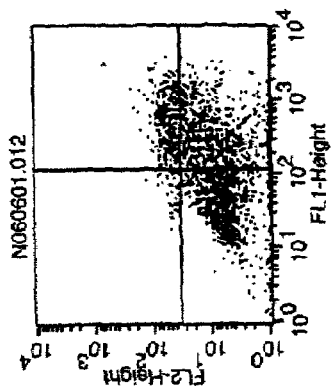
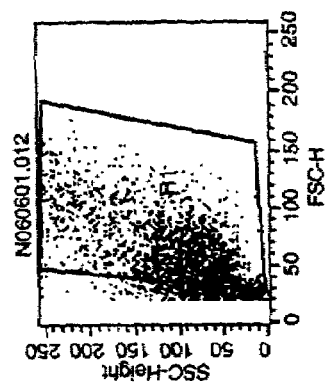
Figure 8I

METHOD FOR INDUCING SELECTIVE CELL DEATH OF MALIGNANT CELLS BY ACTIVATION OF CALCIUM-ACTIVATED POTASSIUM CHANNELS ($K_{CA}$)

BACKGROUND OF THE INVENTION

Throughout the application various publications are referenced in parentheses. The disclosures of these publications in their entireties are hereby incorporated by reference in the application in order to more fully describe the state of the art to which this invention pertains.

1. The Field of the Invention

This invention relates to the medical arts. In particular, it relates to a method of selectively inducing death of malignant cells in vitro and in vivo.

2. Discussion of the Related Art

There are four main types of potassium channels: inverse rectifier potassium channels ($K_{Ir}$); voltage-gated potassium channels ($K_V$); calcium-activated potassium channels ($Ca^{2+}$-activated $K^+$ channel; i.e., $K_{Ca}$); and ATP-sensitive potassium channels ($K_{ATP}$) (Nelson, M. T. and Quayle, J. M., Physiological roles and properties of potassium channels in arterial smooth muscle, Am. J. Physiol. 268(4 Pt 1):C799–822 [1995]). The $K_{Ca}$ and $K_{ATP}$ potassium channels are ubiquitously distributed in tissues including brain capillaries. The $K_{Ca}$ is an important regulator of cerebral blood vessel tone (Nelson M T, Quayle J M. *Physiological roles and properties of potassium channels in arterial smooth muscle*, Am. J. Physiol. 268(4 Pt 1): C799–822 [1995]). The $K_{Ca}$ channel is ubiquitously distributed in tissues as α and β subunits. Its activity is triggered by depolarization and enhanced by an increase in cytosolic calcium dication ($Ca^{2+}$). A local increase in $Ca^{2+}$ is sensed by the extremely sensitive brain α-subunit of the $K_{Ca}$, directed towards the cytoplasm in the cell, that allows a significant potassium cation flux through these channels.

There is growing evidence that membrane ion channels are involved in cell differentiation and proliferation. Potassium channels interfere with a variety of different cell lines derived from breast carcinoma (Wegman et al. Pfuegers Arch. 417:562–570 [1991]), melanoma (Wienhuesal et al. 151:149–157 [1996]), and neuroblastoma (Dubois B and Dubois J M. Cellular Signaling 4:333–339 [1991]). The $K_{Ca}$ channels are known to regulate cell membrane potential and, thus, may have a role in cell proliferation. Biochemical modulation of $K_{Ca}$ channels induces $K^+$ flux causing membrane hyperpolarization affecting the entry of calcium dication. Excessive $K^+$ conductance causes reduction in membrane potential, induces cell death by apoptosis or necrosis in hypoxia and ischemia. Brain tumor cells appear to express immunopositive $K_{Ca}$ channels as studied immunohistochemically with polyclonal anti-$K_{Ca}$ antibody. Further, others have shown that $K_{Ca}$ channels expressed on human glioma cells are highly sensitive to $[Ca^{2+}]_i$ concentration. However, the effect of $K_{Ca}$ channel activation in glioma cell proliferation has not been so far studied.

Treatments directed to the use of potassium channel activators or agonists have been taught for disorders including hypertension, cardiac and cerebral ischemia, nicotine addiction, bronchial constriction, and neurodegenerative diseases, and for increasing the permeability of the blood brain barrier. (Erhardt et al., Potassium channel activators/openers, U.S. Pat. No. 5,416,097; Schohe-Loop et al., 4, 4'-bridged bis-2, 4-diaminoquinazolines, U.S. Pat. No. 5,760,230; Sit et al., 4-aryl-3-hydroxyquinolin-2-one derivatives as ion channel modulators, U.S. Pat. No. 5,922,735; Garcia et al., Biologically active compounds, U.S. Pat. No. 5,399,587; Cherksey, Potassium channel activating compounds and methods of use thereof, U.S. Pat. No. 5,234,947).

Apoptosis is programmed cell death, as signaled by the nuclei in normally functioning human and animal cells, when age or state of cell health and condition dictates. Apoptosis is an active process requiring metabolic activity by the dying cell, often characterized by cleavage of the DNA into fragments that give a so called laddering pattern on gels. Cancerous cells, however, are typically unable to experience the normal cell transduction or apoptosis-driven natural cell death process. Consequently, mechanisms have been sought by which apoptosis may be induced in malignant cells.

Mechanisms of induction of apoptosis in several different cell types and under various physiological conditions have been at least partially studied, and some apoptotic mechanisms appear to be mediated by complex signal transduction pathways involving the phosphorylation and/or dephosphorylation of signal transducing peptides. For example, phosphotyrosine phosphatase inhibitors or activators of protein tyrosine kinase induced apoptosis in B- and T-lymphocytes. (Schieven, G. L., Phosphotyrosine phosphatase inhibitors or phosphotyrosine kinase activators for controlling cellular proliferation, U.S. Pat. No. 5,877,210; Schieven, G. L., Use of phosphotyrosine phosphatase inhibitors for controlling cellular proliferation, U.S. Pat. No. 5,693,627). Also, expression of cytoplasmic Bruton's tyrosine kinase (BTK) has been linked to apoptosis in some cell lines. (Islam, T. C. et al., *BTK mediated apoptosis, a possible mechanism for failure to generate high titer retroviral producer clones*, J. Gene Med. 2(3):204–9 [2000]). On the other hand, signaling by activated Signal Transducers and Activators of Transcription (STATs) may participate in oncogenesis by stimulating cell proliferation and preventing apoptosis. (E.g., Bowman, T. et al., *STATs in oncogenesis*, Oncogene 19(21):2474–88 [2000]; Reddy, E. P., et al., *IL-3 signaling and the role of Src kinases, JAKs and STATs: covert liason unveiled*, Oncogene 19(21):2532–47 [2000]).

Some hypothetical apoptotic mechanisms may be mediated by the activity of certain varieties of potassium channel, but contrary and varied effects indicate that different potassium channels might play different and specific mechanistic roles in apoptosis, if they play any direct role at all. For example, the $K_v1.3$ voltage-gated potassium channel has been implicated in the pathway for Fas-induced apoptosis. (E.g., Gulbins, E. et al., *Ceramide-induced inhibition of T-lymphocyte voltage-gated potassium channel is mediated by tyrosine kinases*, Proc. Natl. Acad. Sci. USA 94(14): 7661–6 [1997]). Expression of $K_{ir}1.1$ potassium channel from an expression vector caused apoptosis in hippocampal neurons. (Nadeau, H. et al., *ROMK1 ($K_{ir}1.1$) cause apoptosis and chronic silencing of hippocampal neurons*, J. Neurophysiol. 84(2):1062–75 [2000]). Also, tumor necrosis factor (TNF)-α-mediated apoptosis of liver cells was dependent on activation of unspecified potassium channels and chloride channels and was further dependent on the presence of calcium dication and protein kinase C activity. (Nietsch, H. H. et al., *Activation of potassium and chloride channels by tumor necrosis factor alpha*, J. Biol. Chem. 275(27): 20556–61 [2000]).

In contrast, the $K_{ATP}$ potassium channel activator cromakalim prevented glutamate-induced or glucose/hypoxia-induced apoptosis in hippocampal neurons. (Lauritzen, I. et al.,*The potassium channel opener (–)-cromakalim prevents glutamate-induced cell death in hippocampal neurons*, J Neurochem, 69(4):1570–9 [1997]). Clofilium, an inhibitor of the $K_v1.5$ delayed rectifier potassium channel, induced apoptosis of human promelocytic leukemia (HL-60) cells. (Choi, B. Y. et al., *Clofilium, a potassium channel blocker, induces apoptosis of human promelocytic leukemia (HL-60) cells via Bcl-2-insensitive activation of caspase-3*, Cancer Lett, 147 (1–2):85–93 [1999]; Malayev, A. A. et al., *Mechanism of clofilium block of the human Kv1.5 delayed rectifier potassium channel*, Mol. Pharmacol. 47(1):198–205 [1995]). Also, $K_v$ inhibitor 4-aminopyridine induced apoptosis in HepG2 human hepatoblastoma cells. (Kim, J. A. et al., $Ca^{2+}$ *influx mediates apoptosis induced by* 4-aminopyridine, *a $K^+$ channel blocker, HepG2 human hepatoblastoma cells*, Pharmacology 60(2):74–81 [2000]).

Thus, links between various types of potassium channels and any particular mechanisms of apoptosis remain unclear, and no role for calcium-activated potassium channels ($K_{Ca}$), in particular, has been suggested.

The ability to induce apoptosis in malignant cells would be especially desirable with respect to malignant tumors, especially tumors of the central nervous system. These malignancies are usually fatal, despite recent advances in the areas of neurosurgical techniques, chemotherapy and radiotherapy.

The glial tumors, or gliomas, comprise the majority of primary malignant brain tumors. Gliomas are commonly classified into four clinical grades, with the most aggressive or malignant form of glioma being glioblastoma multiforme (GBM; also known as astrocytoma grade IV), which usually kills the patient within 6–12 months. (Holland, E. C. et al., *Combined activation of Ras and Akt in neural progenitors induces glioblastoma formation in mice*, Nat. Genet. 25(1): 55–57 [2000]; Tysnes, B. B et al., *Laminin expression by glial fibrillary acidic protein positive cells in human gliomas*, Int. J. Dev. Neurosci. 17(5-6):531–39 [1999]).

GBM tumors are characterized by rapid cell growth and extensive invasion into the surrounding normal brain tissue. GBM tumors are difficult to remove surgically and typically recur locally at the site of resection, although metastases also may occur within the central nervous system. Tumor cell movement within the central nervous system is a complex process that involves tumor cell attachment to the extracellular matrix (ECM) via cell surface receptors, degradation of the ECM by proteolytic enzymes, including serine proteases and matrix metalloproteinases, and subsequent tumor cell locomotion. (Tysnes et al. [1999]; MacDonald, T. J. et al.,*Urokinase induces receptor mediated brain tumor cell migration and invasion*, J. Neurooncol. 40(3):215–26 [1998]; Mäenpää, A. et al., *Lymphocyte adhesion molecule ligands and extracellular matrix proteins in gliomas and normal brain: expression of VCAM-1 in gliomas*, Acta Neuropathol. (Berl.) 94(3):216–25 [1997]). Thus, malignant gliomas overexpress members of the plasminogen activator system and characteristically invade by migrating on ECM-producing white matter tracts and blood vessel walls. (Tysnes et al. [1999]; Colognato, H. and Yurchenco, P. D., *Form and function: the laminin family of heterotrimers*, Dev. Dyn. 218(2):213–34 [2000]).

Despite a wealth of molecular biological, biochemical and morphological information that is available today on gliomas, the prognosis with treatment has not significantly changed in the last two decades and remains among the worst for any kind of malignancy. (E.g., Shapiro, W. R., Shapiro, J. R., *Biology and treatment of malignant glioma*, Oncology 12:233–40 [1998]; Thapar, K. et al., *Neurogenetics and the molecular biology of human brain tumors*, In: *Brain Tumors*, Edit. Kaye A H, Laws E R, pp.990. [1997]).

In particular, there are no standard therapeutic modalities that can substantially alter the prognosis for patients with malignant glial tumors of the brain, cranium, and spinal cord. Although intracranial tumor masses can be debulked surgically, treated with palliative radiation therapy and chemotherapy, the survival associated with intracranial glial tumors, for example, a glioblastoma, is typically measured in months.

The present invention provides a much needed method of inducing apoptosis in glioma cells, in vitro and in vivo, that employs activators of calcium-activated potassium channels. This and other benefits of the present invention are described herein.

SUMMARY OF THE INVENTION

The disclosed invention is directed to a method of inducing apoptosis in a malignant cell, such as a glioma cell. The method involves treating the malignant cell with a calcium-activated potassium channel ($Ca^{2+}$-activated $K^+$ channel; i.e., $K_{Ca}$) activator, such as, but not limited to NS-1619, which is administered under conditions and in an amount sufficient to induce apoptosis of the cell, i.e., programmed cell death. In contrast, normal cells, such as normal human brain endothelial cells and human fetal astrocytes, are insensitive to the $K_{Ca}$ activator and are not adversely affected by the treatment. Hence the present invention relates to a method of selectively inhibiting the proliferation of malignant cells compared to non-malignant cells in a mixed population of malignant and non-malignant cells, whether in vitro or in vivo. The method involves administering to the mixed population of malignant and non-malignant cells a calcium-activated potassium channel activator in an amount sufficient to induce apoptosis of at least a plurality of malignant cells compared to non-malignant cells, thereby selectively inhibiting the proliferation of malignant cells.

Since the present invention is capable of selectively targeting malignant cells, whether in vitro or in vivo, the present invention also relates to a method of inhibiting the growth of a malignant tumor, such as a glial tumor, in a mammalian subject. The method involves administering to a mammalian subject having a malignant tumor, which comprises a malignant cell, a calcium-activated potassium channel activator under conditions and in an amount sufficient to induce apoptosis of the cell, thereby inhibiting growth of the tumor.

Thus, the invention provides a useful addition to the pharmaceutical anti-cancer armamentarium, especially for treating patients who do not respond well to commonly used chemotherapeutic agents. Moreover, the administration of $K_{Ca}$ activators is not associated with the debilitating systemic side effects typical of the cytotoxic agents currently used in anti-cancer chemotherapy.

Useful kits are also provided for facilitating the practice of the inventive methods.

These and other advantages and features of the present invention will be described more fully in a detailed description of the preferred embodiments which follows.

BRIEF DESCRIPTION OF THE DRAWINGS

FIG. 4 shows a differential sensitivity to NS-1619 at 50 µg/mL among primary human GBM, astrocytoma, and U373MG glioma cells. Relative insensitivity of normal cell lines HBMVEC and HFA is also shown.

FIG. 5 illustrates the in vitro effect of $K_{Ca}$ activator NS-1619 on in vitro U87 cell proliferation, as measured by apoptosis assay and FACS analysis. FIG. 5B shows the effect on U87 cells of 50 µg/nL NS-1619 ; and FIG. 5C shows the effect of 5 µM staurosporin (positive control).

DETAILED DESCRIPTION OF THE PREFERRED EMBODIMENTS

Figure 1:
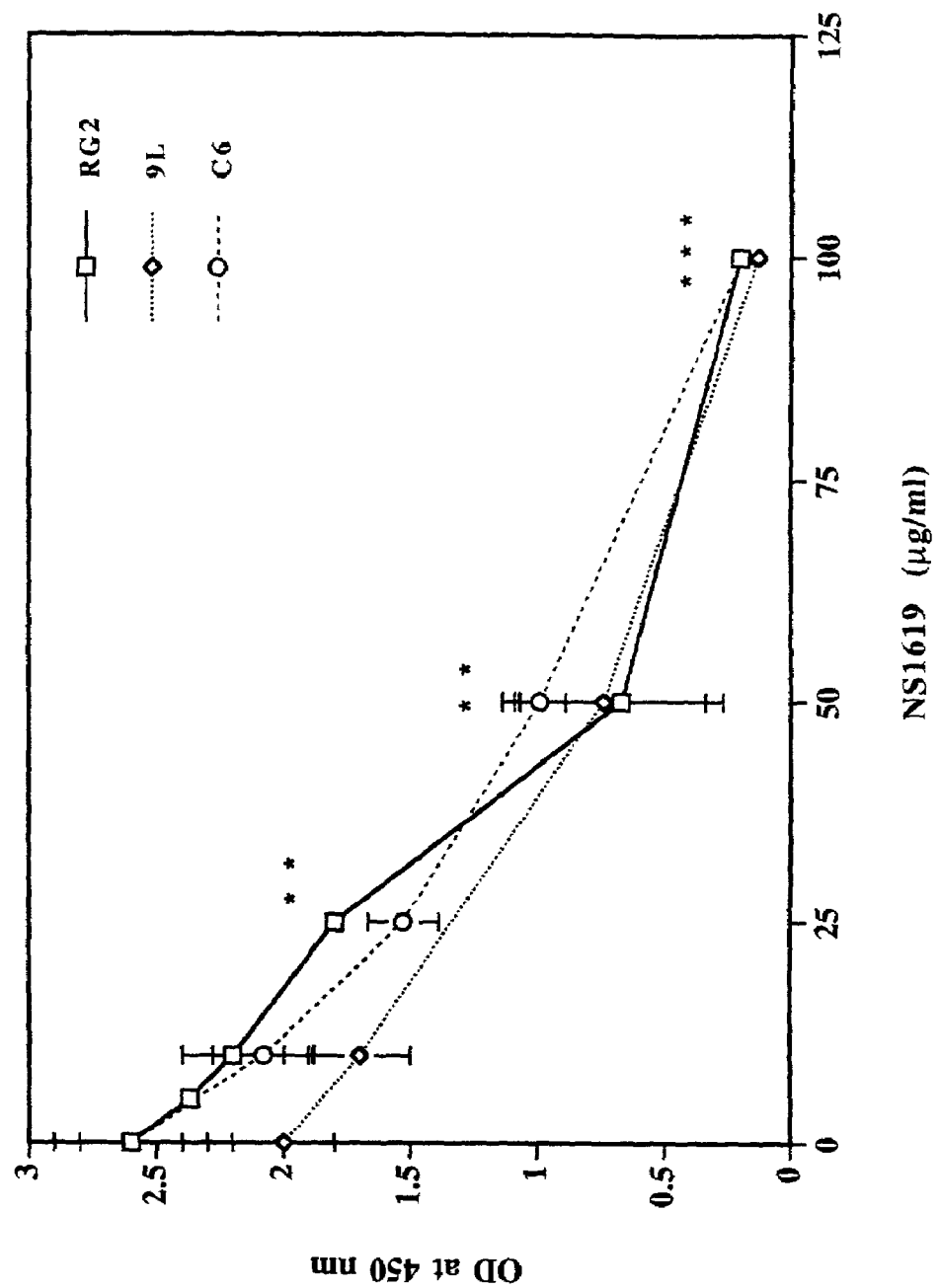
FIG. 1 shows in vitro effect of $K_{Ca}$ activator NS-1619 on in vitro cell proliferation, as measured by optical density (OD) at 450 nm wavelength, by rat glioma cells (RG2, C6, and 9L). =P<0.01;*=P<0.001.

The present invention relates to a method of inducing apoptosis in malignant cells, such as glioma cells, whether in vitro or in vivo. Thus, the present invention also relates to a method of inhibiting the growth of a malignant tumor in a mammalian subject.

A malignant tumor includes, but is not limited to, a glioma, a glioblastoma, an oligodendroglioma, an astrocytoma, an ependymoma, a primitive neuroectodermal tumor, an atypical meningioma, a malignant meningioma, a neuroblastoma, a sarcoma, a melanoma, a lymphoma, or a carcinoma. The malignant tumor can be contained within in the skull, brain, spine, thorax, lung, abdomen, peritoneum, prostate, ovary, uterus, breast, stomach, liver, bowel, colon, rectum, bone, lymphatic system, or skin, of the mammalian subject.

Among malignant tumors for which the inventive methods are effective are gliomas, which include any malignant glial tumor, i.e., a tumor derived from a transformed glial cell. A glial cell includes a cell that has one or more glial-specific features, associated with a glial cell type, including a morphological, physiological and/or immunological feature specific to a glial cell (e.g. astrocyte or oligodendrocyte), for example, expression of the astroglial marker fibrillary acidic protein (GFAP) or the oligodendroglial marker O4. Gliomas include, but are not limited to, astrocytoma grade II, anaplastic astrocytoma grade III, astrocytoma with oligodendrogliomal component, oligodendroglioma, and glioblastoma multiforme (GBM; i.e., astrocytoma grade IV).

The inventive methods are useful in treating malignant cells originating from, or found in, any mammal, including a human, non-human primate, canine, feline, bovine, porcine or ovine mammal, as well as in a small mammal such as a mouse, rat, gerbil, hamster, or rabbit.

The method of inducing apoptosis in a glioma cell involves treating the cell with a calcium-activated potassium channel ($K_{Ca}$ activator, under conditions and in an amount sufficient to induce apoptosis of the cell, i.e., programmed cell death.

Examples of useful $K_{Ca}$ activators include 1,3-dihydro-1-[2-hydroxy-5-(trifluoromethyl)phenyl]-5-(trifluoromethyl)-2H-benzimidazol-2-one (NS-1619, a specific large conductance $K_{Ca}$ activator; RBI, Natick, Mass.), or 1-ethyl-2-benzimidazolinone (1-EBIO). Also included among useful $K_{Ca}$ activators is the vasodilator bradykinin (Arg-Pro-Pro-Gly-Phe-Ser-Pro-Phe-Arg), or a polypeptide bradykinin analog, such as receptor mediated permeabilizer (RMP)-7 or A7 (e.g., Kozarich et al., U.S. Pat. No. 5,268,164 and PCT Application No. WO 92/18529). Other useful analogs of bradykinin include related peptide structures which exhibit the same properties as bradykinin but have modified amino acids or peptide extensions on either terminal end of the peptide. For example, such bradykinin analogs include [phe.sup.8 (CH.sub.2-NH) Arg.sup.9]-bradykinin, N-acetyl [phe.sup.8 (CH.sub.2-NH-Arg.sup.9] bradykinin and desArg9-bradykinin. For the purposes of the present invention, other useful $K_{Ca}$ activators include soluble guanylyl cyclase activators, such as, metalloporphyrins (e.g., zinc or tin protoporphyrin IX), YC-1 (a benzyl indazole derivative), or guanylyl cyclase activating proteins (GCAPs).

Included among useful $K_{Ca}$ channel activators are pharmaceutically acceptable molecular conjugates or salt forms that still have activity as $K_{Ca}$ channel activators. Examples of pharmaceutically acceptable salts comprise anions including sulfate, carbonate, bicarbonate, nitrate, or the like. Other embodiments of pharmaceutically acceptable salts contain cations, such as sodium, potassium, magnesium, calcium, or the like. Other embodiments of useful potassium channel agonists are hydrochloride salts.

In accordance with the inventive method, "administering" the $K_{Ca}$ channel activator to a cell, or population of cells, includes exposing the cell to the activator, applying the activator to the cell, giving the activator to the cell, treating or bathing the cell with the activator, or, particularly for in vitro embodiments, adding the activator to a liquid, semi-solid, or solid cell culture medium containing or supporting the cell. Preferably, quantities of $K_{Ca}$ channel activator sufficient to induce apoptosis of the malignant cell, in vitro, including under normal physiological conditions (e.g., normal physiological pH, oxygenation, and nutrient repletion), generally range from about 5 μg/mL to about 100 μg/mL, and more preferably about 50 μg/mL to about 100 μg/mL, but sufficient quantities appropriate for particular malignant cell types are readily determined by routine in vitro screening methods.

In accordance with the inventive method, applied in vivo, the calcium-activated potassium channel activator is preferably administered to the mammalian subject by a transvascular delivery route, for example, by intravenous or intra-arterial injection or infusion. For treating an intracranial tumor, the calcium-activated potassium channel activator is preferably administered to the mammalian subject by intra-carotid infusion.

In other preferred in vivo embodiments, administration of the $K_{Ca}$ activator to the mammalian subject, for delivery to a malignant tumor, is by intratumoral injection through a surgical incision, for example, through a craniotomy for a brain tumor. Typically, but not necessarily, surgical debulking of the tumor is done, if possible, before injection of the $K_{Ca}$ activator into the remaining tumor mass containing malignant cells. Also for treating a brain tumor, another preferred delivery method is stereotactic injection of the $K_{Ca}$ activator into the malignant tumor at a site having pre-established coordinates.

For in vivo embodiments of the inventive methods, the amount of $K_{Ca}$ activator to be administered ranges from 0.075 to 1500 micrograms per kilogram body mass. For humans the range of 0.075 to 150 micrograms per kilogram body mass is most preferred. This can be administered in a bolus injection, but is preferably administered by infusion over a period of one to thirty minutes, and most preferably during a period of one to about fifteen minutes. For example, in rats, a dose rate of about 0.75 to about 100 μg kg$^{-1}$ min$^{-1}$ most suitable. At dose rates above about 200 μg kg$^{-1}$ min$^{-1}$ a concomitant fall in blood pressure has been observed In humans, effective dose rates are about 0.075 to about 15 μg kg$^{-1}$ min$^{-1}$, with cautious monitoring of blood pressure being advised. The practitioner skilled in the art is also cautious in regulating the total infusion volume, rate of liquid infusion, and electrolyte balance to avoid adverse physiological effects related to these.

For example, for delivery by intravascular infusion or bolus injection into a mammal, such as a human, the $K_{Ca}$ activator is preferably in a solution that is suitably balanced, osmotically (e.g., about 0.15 M saline) and with respect to pH, typically between pH 7.2 and 7.5; preferably the solution further comprises a buffer, such as a phosphate buffer (e.g., in a phosphate buffered saline solution). The solution is formulated to deliver a dose of about 0.075 to 1500 micrograms of $K_{Ca}$ activator per kilogram body mass in a pharmaceutically acceptable fluid volume over a maximum of about thirty minutes. For human subjects, the solution is preferably formulated to deliver a dose rate of about 0.075 to 150 micrograms of potassium channel agonist per kilogram body mass in a pharmaceutically acceptable fluid volume over a period of up to about thirty minutes.

In accordance with the inventive method, adminstration of the $K_{Ca}$ activator is preferably, but not necessarily, repeated, as described hereinabove, for two to three consecutive days.

Some useful $K_{Ca}$ channel activators, such as NS-1619, are not easily dissolved in water; in preparing these agents for administration, a suitable and pharmaceutically acceptable solvent, such as ethanol (e.g., 25% v/v ethanol or higher ethanol concentrations), can be used to dissolve the $K_{Ca}$ potassium channel activator, prior to further dilution with an infusion buffer, such as PBS. The skilled practitioner is cautious in regulating the final concentration of solvent in the infusion solution to avoid solvent-related toxicity. For example, a final ethanol concentration in an infusion solution up to 5–10% (v/v) is tolerated by most mammalian subjects with negligible toxicity.

While the inventive method does not depend on any particular mechanism or signal transduction pathway by which apoptosis is induced, it is thought that administration of the potassium channel activator increases potassium flux through calcium-activated potassium channels in the cell membranes of malignant cells and in endothelial cell membranes of the capillaries and arterioles delivering blood to malignant tumors. In practicing the inventive methods, it is not necessary to measure potassium channel activity (i.e., potassium cation flux therethrough). But the skilled artisan is aware that potassium flux can be measured by any suitable method, for example, by measuring cellular uptake of $^{42}$K$^+$ or $^{201}$Tl$^+$ or channel conductance using patch-clamp or microelectrode devices. (e.g., T. Brismar et al., *Thallium-201 uptake relates to membrane potential and potassium permeability in human glioma cells*, Brain Res. 500(1–2):

30–36 [1989]; T. Brismar et al., *Mechanism of high K⁺ and Tl⁺ uptake in cultured human glioma cells*, Cell Mol. Neurobiol. 15(3):351–60 [1995]; S. Cai et al., *Single-channel characterization of the pharmacological properties of the K(Ca2+) channel of intermediate conductance in bovine aortic endothelial cells*, J. Membr. Biol. 163(2):147–58 [1998]).

The invention also relates to a kit for inducing apoptosis in a malignant cell in accordance with the inventive methods described herein. The kit is an assemblage of materials or components, including a $K_{Ca}$ potassium channel activator in a pharmaceutically acceptable formulation, as described above. In addition, the kit contains instructions for using the $K_{Ca}$ activator in accordance with the inventive methods. Optionally, the kit also contains other components, such as, diluents, buffers, pharmaceutically acceptable carriers, pipetting or measuring tools or paraphernalia for injection or infusion, for example syringes, stents, catheters, infusion lines, clamps, and/or infusion bags/bottles, which can contain a pharmaceutically acceptable formulation of the $K_{Ca}$ activator. The pharmaceutically acceptable formulation contains the $K_{Ca}$ activator and can also optionally contain one or more pharmaceutically acceptable carrier(s). As used herein, the term "acceptable carrier" encompasses any of the standard pharmaceutical carriers. The carrier can be an organic or inorganic carrier or excipient, such as water and emulsions such as an oil/water or water/oil emulsion, and various types of wetting agents. The active ingredient(s) can optionally be compounded in a composition formulated, for example, with non-toxic, pharmaceutically acceptable carriers for injections, infusions, tablets, pellets, capsules, solutions, emulsions, suspensions, and any other form suitable for use. Such carriers also include glucose, lactose, gum acacia, gelatin, mannitol, starch paste, magnesium trisilicate, talc, corn starch, keratin, colloidal silica, potato starch, urea, medium chain length triglycerides, dextrans, normal saline, phosphate buffered saline and other carriers suitable for use in manufacturing preparations, in solid, semisolid, or liquid form. In addition auxiliary, stabilizing, thickening and coloring agents and perfumes can be used as appropriate.

Optionally, the kit also contains other useful components. The materials or components assembled in the kit can be provided to the practitioner stored in any convenient and suitable ways that preserve their operability and utility. For example the components can be dissolved, dehydrated, or lyophilized form; they can be provided at room, refrigerated or frozen temperatures.

The exact nature of the components configured in the inventive kit depends on its intended purpose. For example, some embodiments of the kit are configured for the purpose of treating cultured mammalian cells. Other embodiments are configured for the purpose of treating mammalian cells in vivo, i.e., for treating mammalian subjects in need of treatment, for example, subjects with malignant tumors. Preferred embodiments are directed to treating gliomas. In a most preferred embodiment, the kit is configured particularly for the purpose of treating human subjects.

Instructions for use are included in the kit. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like, typically for an intended purpose.

The components are typically contained in suitable packaging material(s). As employed herein, the phrase "packaging material" refers to one or more physical structures used to house the contents of the kit, such as, the $K_{Ca}$ activator. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass or plastic vial or ampoule. The packaging material generally has an external label which indicates the contents and/or purpose of the kit and/or its components.

The foregoing descriptions of the methods and kits of the present invention are illustrative and by no means exhaustive. The invention will now be described in greater detail by reference to the following non-limiting examples.

EXAMPLES

Example 1

Methods

Cells

Primary cell lines were prepared from human gliomas (glioblastoma multiforme [GBM] or astrocytoma) or established rat glioma cell lines (RG2, C6 and 9L) were used. Cultured human normal cell lines, brain microvessel endothelial cells (HBMVEC), or fetal astrocytes were used.

Cell Proliferation Assay

Cells ($5 \times 10^4$ cells) were cultured in each well of 96-well microtiter culture plates and were allowed to achieve confluency to form a monolayer of cells in each well. For dose response studies cells were incubated with different concentrations (1–100 μg/mL) of NS-1619 or minoxidil sulfate for 4 hours at 37° C. in a $CO_2$ (5%) incubator. Cells washed twice carefully with respective medium, and allowed to incubate overnight at 37° C. under 5% $CO_2$. The following day, cells were incubated with WST-1 reagent (Boehringer Mannheim) at 37° C. in a $CO_2$ (5%) incubator for 60–90 minutes, and optical density at 450 nm was measured with a 96-well plate reader. The magnitude of OD indicated the number of viable cells, greater the OD, higher the number of viable cells, correlated a standard curve of cell numbers.

In Vitro Apoptosis Studies in Human Cells

Human glioma cells (U-87) and HBMVECells were seeded into a 25-mL tissue-culture flask. After 24 h (about 60–70% confluencey), cells were treated with either NS-169 (50 or 100 micrograms/mL) or staurosporine (positive control; 5 μM), a known inducer of apoptosis (Tamaoki, T., et al., *Staurosporine, a potent inhibitor of phospholipid/$Ca^{++}$ dependent protein kinase*, Biochem. Biophys. Res. Commun. 135: 397–402 [1986]; Matsumoto, H., and Sasaki, Y., *Staurosporine, a protein kinase C inhibitor interferes with proliferation of arterial smooth muscle cells*, Biochem. Biophys. Res. Commun. 158:105–109 [1989]). U-87 cells were returned to the $CO_2$ incubator and incubated overnight. The following day, cells were washed twice with fresh growth medium and cells prepared for FACS analysis as described hereinbelow.

Apoptosis Assay

The changes in plasma membrane are one of the earliest events in cell death. In apoptotic cells the membrane phospholipid phosphatidylserine (PS) is translocated from the inner to the outer leaflet of the cell membrane in the early phases of apoptosis. Annexin V is a $Ca^{2+}$-dependent, phospholipid-binding protein that binds to PS with high affinity.

Consequently, Annexin V (PharMingen) conjugated to a label, such as fluorescein isothiocyanate (FITC) or biotin, serves as a sensitive probe for flow cytometry analysis of cells that are undergoing apoptosis. The manufacturer's suggested protocol was followed. (PharMingen; Vermes, I. et al., *A novel assay for apoptosis. Flow cytometric detection of phosphatidylserine expression on early apoptotic cells using fluorescein labelled Annexin V*, J. Immunol. Meth. 184:39–51 [1995]). Concurrently, propidium iodide is typically used as a standard flow cytometric viability probe, because the intact cell membranes of viable cells exclude propidium iodide, whereas the cell membranes of dead and damaged cells are permeable to propidium iodide. Cells that stain positive for Annexin V and negative for propidium iodide are undergoing apoptosis; cells that stain positive for both Annexin V and propidium iodide are either at the end stage of apoptosis, are undergoing necrosis, or are already dead; and cells that stain negative for both Annexin V-biotin and propidium iodide are alive and not undergoing measurable apoptosis. Briefly, the cells were washed twice with cold PBS and then resuspended in 1× binding buffer (10 mM HEPES/NaOH, pH 7.4, 140 mM NaCl, 2.5 mM $CaCl_2$; 4° C.) at a concentration of about $1\times10^6$ cells/mL. A 100-µL aliquot of cell suspension was transferred to 5-mL culture tubes, and 2.5 µL of Annexin V-FITC and 2.5-µL of propidium iodide (PharMingen) were added to each tube. The cell suspensions were gently mixed and incubated for 15 min at room temperature in the dark, after which 400 µL of binding buffer was added to each tube of cells. The cells were then washed once with 1×binding buffer. Analysis by flow cytometry was then conducted immediately, and no later than within one hour. The resulting analytic FACS graphs were typically divided into four quadrants wherein the upper right (UR) quadrant represented the number of necrotic cells; the lower left (LL) quadrant represented the number of viable cells; the lower right (LR) quadrant represented the number of apoptotic cells; and the upper left (UL) represented cells of an intermediate category, which generally represents cell debris and DNA fragments. The percentage of gated events in each quadrant was used to determine the total percentage of apoptotic and necrotic cells in each cell suspension.

Protein Tyrosine Kinase (PTK) Assay

A PTK assay kit (The Oncogene Research Products, Boston, Mass.) was used to determine the presence and relative amounts of protein kinase activity in tissue cytosols and cell extracts. Briefly, $1\times10^4$ RG2 cells seeded in a 50-mL culture flask, and allowed to achieve confluency to form a monolayer at 37° C. in a $CO_2$ incubator. Protein tyrosine kinase was extracted from RG2 cells as suggested by the kit's manufacturer.

Briefly, RG2 cells were harvested after trypsinization, and cells were pelleted by centrifugation. Cells were resuspended with extraction buffer (20 mM Tris, pH 7.4, 50 mM NaCl, 1 mM EDTA, 1 mM EGTA, 0.2 mM PMSF, 1 µg/mL pepstatin, 0.5 µg/mL leupetin, 0.2 mM $Na_3VO_4$, 5 mM mercaptoethanol, 0.1% Triton X-100), and cells were lysed using a cell homogenizer. After centrifugation, supernatant was separated from the pellet for PTK assay. The supernatant was treated with superoxide dismutase. Pervanadate (100 mM) was used in the PTK assay to inhibit ATPase activity, and protein concentration was determined by Lowry's method using a Bio-Rad protein assay kit. Supernatant containing 50 µg protein was incubated, either with or without NS-1619 or valinomycin at various concentrations (1–50 µM), at room temperature.

Assay for PTK activity in RG2 cell-lysates was then performed according to the protocol supplied by the PTK assay kit's manufacturer. After adding the stop solution, absorbance measured in each well at 450 nm using a Spectramax Plus (Molecular Devices, Sunnyvale, Calif.).

In Vivo Studies in Implanted Tumors

A rat tumor model, which consisted of intracranially implanted RG2 cells (rat glioma cell line) in Wistar rats, was employed to investigate whether any of several potassium channel activators induce selective apoptosis of tumor cells in vivo.

The techniques for RG2 cell propagation and maintenance in tissue culture have been described (Sugita, M. and Black, K. L., *Cyclic GMP-specific phosphodiesterase inhibition and intracarotid bradykinin infusion enhances permeability into brain tumors*, Cancer Res. 58(5):914–20 [1998]; Inamura et al. [1994]; Nakano, S. et al., *Increased brain tumor microvessel permeability after intracarotid bradykinin infusion is mediated by nitric oxide*, Cancer Res. 56(17):4027–31 [1996]). Briefly, RG2 cells derived from a rat glioma are kept frozen until use, then are thawed and maintained in a monolayer culture in F12 medium with 10% calf serum.

The Wistar rats (approximately 140–160 g body weight) were anesthetized with intra-peritoneal ketamine (50 mg/kg), and glial cells ($1\times10^5$) were implanted into the right hemisphere, but not the contralateral hemisphere, by intracerebral injection suspended in 5 µL F12 medium (1–2% methylcellulose) by a Hamilton syringe. The implantation coordinates were 3-mm lateral to the bregma and 4.5 mm deep to the dural surface.

On the seventh day after tumor implantation, rats were anesthetized, the internal carotid artery was cannulated with P-50 polyethylene catheter, and the catheter was exteriorized so that the catheter was placed on the back of the rat for multiple infusions. Two rats were used for this study. One rat was given two doses of NS-1619 (20 µg/kg) on days 7 and 9, or 5 µM staurosporine on day 9, while another rat was administered vehicle (PBS, pH 7.4+1% v/v ethanol) as a control.

Ten days after RG2 implantation, the rats were euthanized under anesthesia and tumor and contralateral tumor tissues were carefully dissected for preparation of a single-cell suspension. Tissues were gently minced with a sharp surgical blade, using 18G and 22G needles; a single cell suspension was prepared by repeated aspirations with a syringe. Cells then were centrifuged at 1000 rpm for 5 minutes, and the supernatant was discarded. The resulting pellet was resuspended with 1–2 mL of PBS, and was washed twice in a similar manner. The final pellet of cells was resuspended in 100 µL 1×binding buffer as described hereinabove (supplied by PharMingen), was mixed well with 2.5 µL each of propidium iodide and FITC-conjugated Annexin V antibody, and was then incubated for 15 minutes in darkness. Finally, 400 µL of 1×binding buffer was added to the cell suspension and FACS analysis was performed as described hereinabove.

Immunohistochemical Detection of $K_{Ca}$ Channels

Brain sections (12 µm thick) obtained from the permeability studies were incubated with 1:100 dilution of affinity-purified $K_{Ca}$ channel antibody (Alomone Labs, Jerusalem, Israel) for 1 hour, and biotinylated horse anti-mouse immunoglobin (Vector Laboratories, Burlingame, Calif.) for 30 minutes. After washing 3 times with PBS, the peroxidase sites were visualized using an avidin:biotinylated enzyme complex (ABC) kit.

Example 2

Results

Cell Proliferation Inhibited by $K_{Ca}$ Activator

Figure 2:
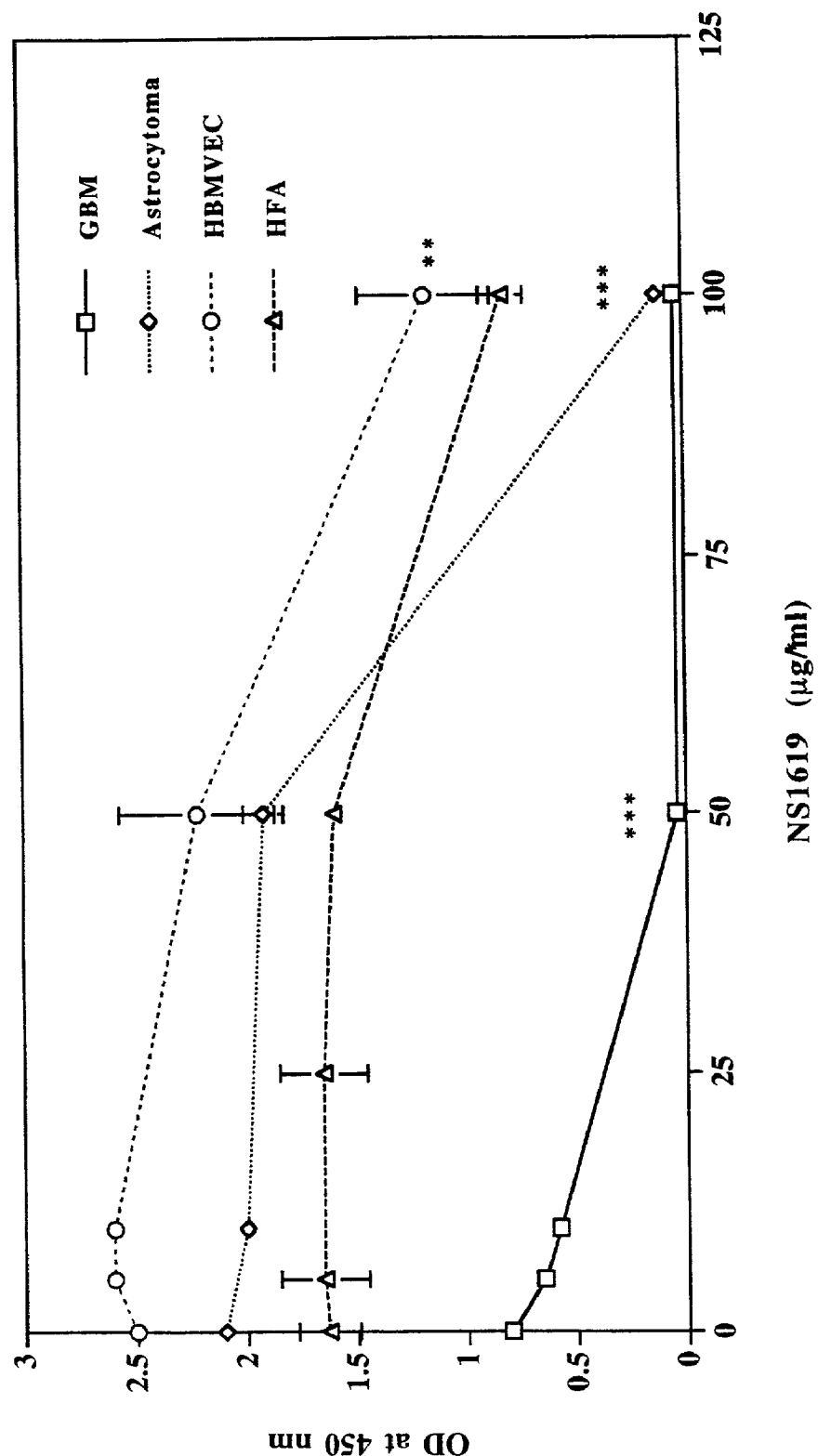
FIG. 2 shows in vitro effect of $K_{Ca}$ activator NS-1619 on in vitro cell proliferation, as measured by optical density (OD) at 450 nm wavelength, by primary human glioma cell lines (GBM and astrocytoma) or human normal cell lines (brain microvessel endothelial cells [HBMVEC], or fetal astrocytes [HFA]). =$P<0.01$; *=$P<0.001$.

Cell proliferation assays were conducted, in vitro, as described herein, with rat glioma cells (RG2, C6 and 9L) or human normal cell lines, brain microvessel endothelial cells (HBMVEC), or fetal astrocytes (HFA). Results showed that $K_{Ca}$ activator (NS-1619) significantly blocks cell proliferation selectively in the rat glioma cell lines in a dose-dependent manner (FIG. 1). Similarly, NS-1619 significantly blocked cell proliferation selectively in primary human glioma cell lines (GBM and astrocytoma) in a dose-dependent manner without affecting the normal HBMVEC and HFA cell lines (FIG. 2). All of the rat and human malignant cells studied, as well as normal cells, were insensitive to $K_{ATP}$ channel agonist, minoxidil sulfate (data not shown).

Figure 3:
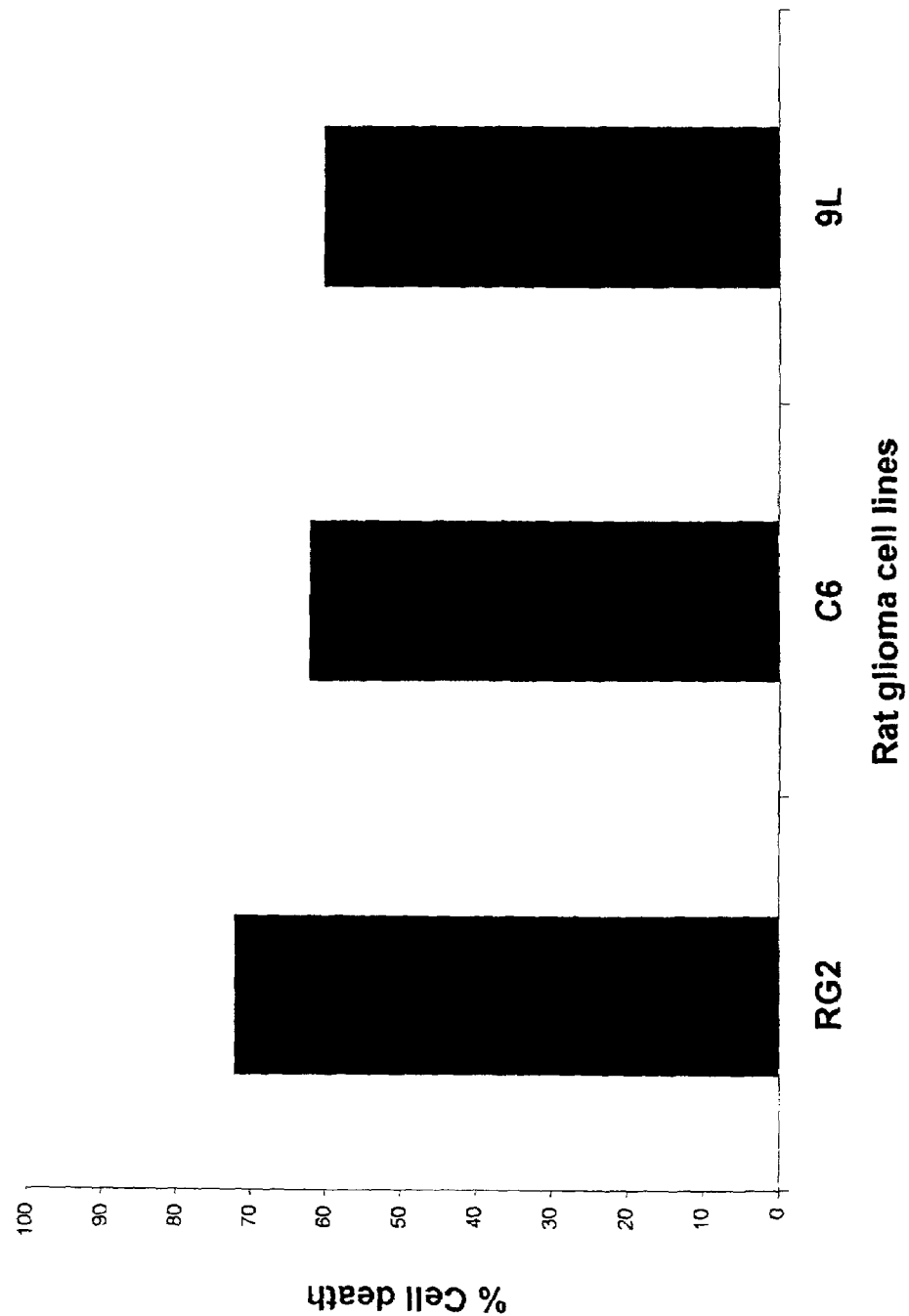
FIG. 3 illustrates a differential sensitivity to NS-1619 (50 µg/mL) that was observed among rat glioma cell lines RG2, C6, and 9L.

FIG. 3 illustrates that a differential sensitivity to NS-1619 (50 µg/mL) that was observed among rat glioma cell lines RG2, C6, and 9L, with RG2 being most sensitive (70% cell death). A similar differential sensitivity to NS-1619 at 50 µg/mL was observed with primary human GBM, astrocytoma, and U373MG glioma cell lines, GBM being most sensitive (90% cell death; FIG. 4). Normal cell lines HBMVEC and HFA were insensitive to NS-1619 at 50 µg/mL concentration (FIG. 4).

Apoptosis Induction by $K_{Ca}$ Activator

Figure 5A:
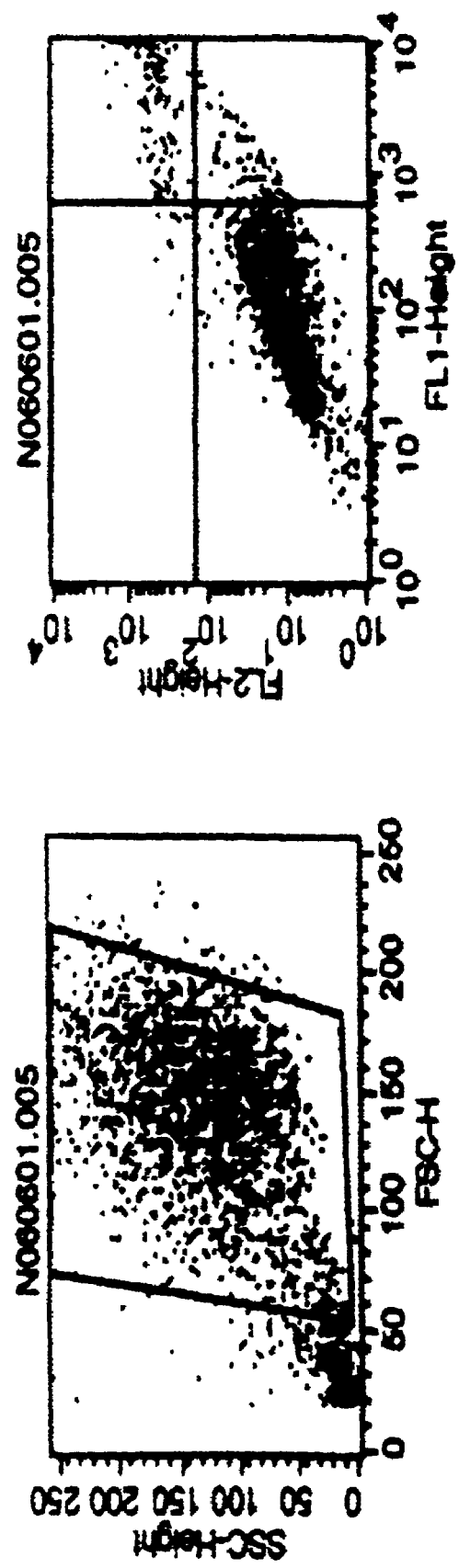
FIG. 5A shows the effect of vehicle (negative control)

FACS analysis showed that administration of NS-1619 (50 µg/mL) to U87 cells resulted in 21% apoptotic cells and 14% necrotic cells (FIG. 5A), compared to a vehicle (negative control) that had 5% apoptotic and 7% necrotic cells (FIG. 5A), U87 cells exposed to 5 µM staurosporin (positive control), a known inducer of apoptosis, showed 31% apoptotic cells and 27% necrotic cells (FIG. 5C).

Figure 6A:
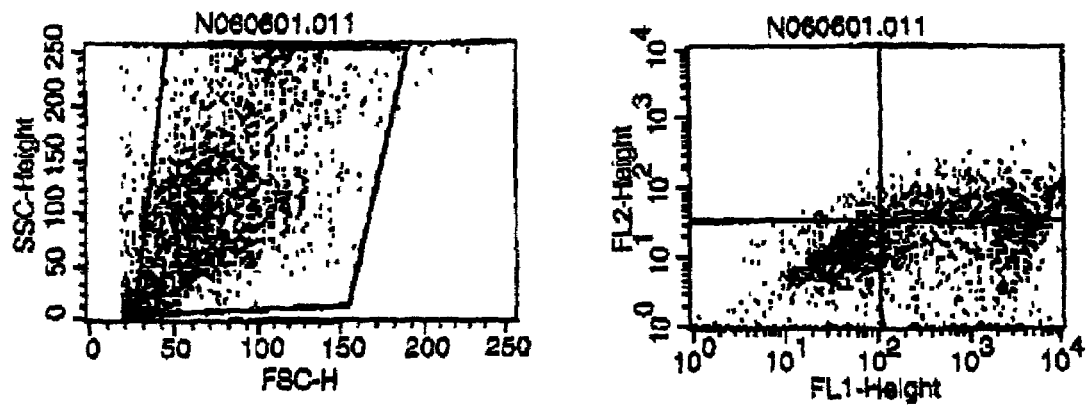
FIG. 6 illustrates FACS detection of apoptosis induction by NS-1619 (50 µg/mL) in malignant rat cells in vitro, compared to untreated controls: RG2 cells (NS-1619-treated [FIG. 6A] and control [FIG. 6B]); C6 cells (NS-1619-treated [FIG. 6C] and control [FIG. 6D]); and 9L cells (NS-1619-treated [FIG. 6E] and control [FIG. 6F]). SSC-Height=size scattering height, which indicates degree of granularity or complexity of cells; FSC-Height=forward scattering height, which indicates size of events or cells; PI=magnitude of propidium iodide staining; annexin V-FITC=magnitude of annexin V-fluorescein isothiocyanate staining.
Figure 6B:
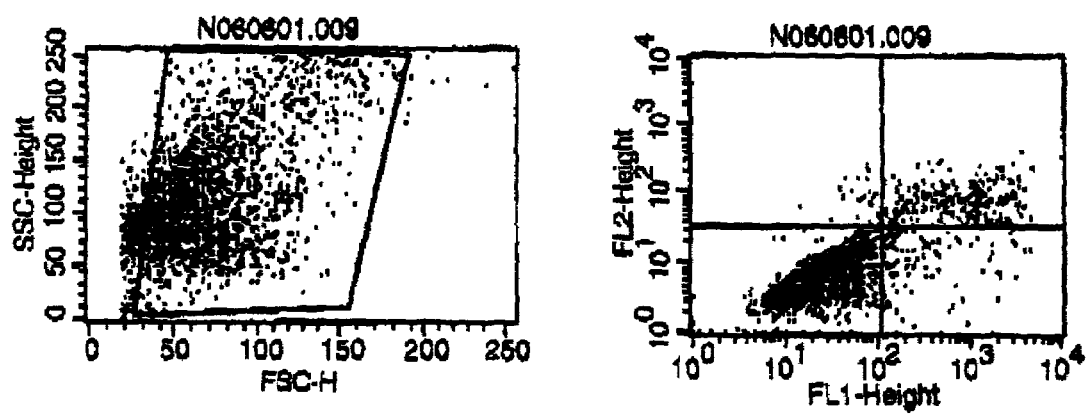

Similarly, FACS analysis showed that administration of NS-1619 (50 µg/mL) to malignant RG2 cells greatly increased apoptosis (29%) and necrosis (29%)(FIG. 6A), compared to the percentage of apoptotic (5%) and necrotic (11%) cells in untreated RG2 cell suspensions (FIG. 6B). Similar results were obtained with NS-1619-treated malignant C6 cells (25% apoptotic, 35% necrotic C6 cells; FIG. 6C) and 9L cells (42% apoptotic, 32% necrotic 9L cells; FIG. 6E), compared to 5% apoptotic and 10% necrotic among untreated C6 cells (FIG. 6D), and 15% apoptotic and 7% necrotic among untreated 9L cells (FIG. 6F).

Figures 7A, 7B:
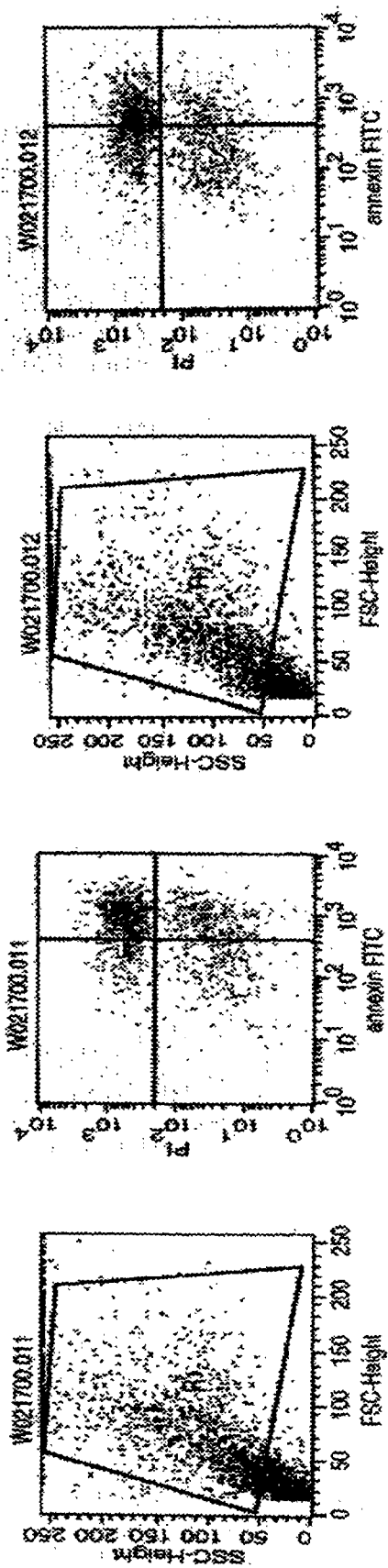
FIG. 7 illustrates FACS detection of apoptosis induction by NS-1619 (50 µg/L) in malignant human cells in vitro (GBM primary cell line), compared to untreated controls, and normal (i.e., non-malignant) human cells (HBMVEC): GBM cells (NS-1619-treated [FIG. 7A] and control [FIG. 7B]); HBMVEC cells (NS-1619-treated [FIG. 7C] and control [FIG. 7D]). SSC-Height=size scattering height, which indicates degree of granularity or complexity of cells; FSC-Height=forward scattering height, which indicates size of the event; PI=magnitude of propidium iodide staining; annexin V-FITC=magnitude of annexin V-fluorescein isothiocyanate staining.

FACS analysis shows that NS-1619 (50 µg/mL) treatment greatly increased apoptosis (24%) and necrosis (49%) among primary human GBM cells (FIG. 7A), compared to 12% apoptotic and 36% necrotic cells among untreated GBM primary cells (FIG. 7B). However, NS-1619 (50 µg/mL) treatment did not significantly induce either apoptosis or necrosis in non-malignant HBMVEC (4% apoptosis in both treated and vehicle controls; FIG. 7C and FIG. 7D).

Figures 8C, 8D:
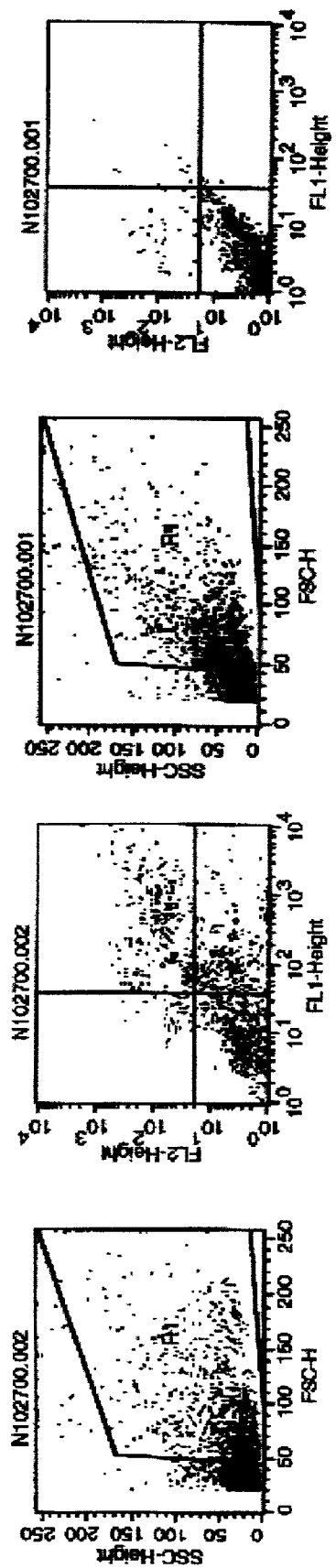
FIG. 8C) and normal contralateral brain tissue of the same rat treated with NS-1619 (FIG. 8D); (100 µg NS-1619/kg/day.
Figure 8E:
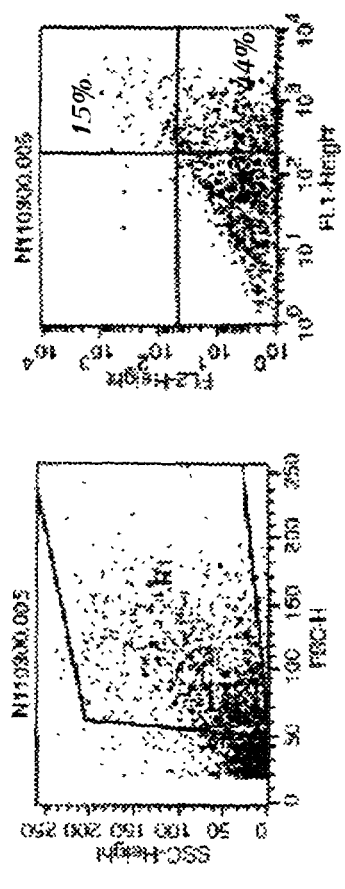
FIG. 8E) and normal contralateral brain tissue of the same rat (FIG. 8F); 100 µg NS-1619/kg/day.
Figure 8F:
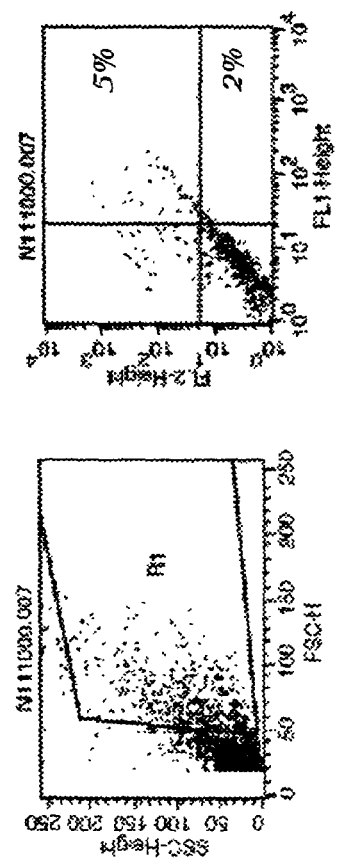
FIG. 8 illustrates FACS detection of apoptosis induction by intracarotid (100 µg NS-1619/kg/min for 15 minutes, flow rate=0.0823 mL/min) injection of NS-1619 in Wistar rats having implanted RG2 gliomas, in vivo, compared to untreated controls: glioma tumor after 2 daily infusions of vehicle ([3.2 mL PBS+0.5% ethanol]/kg body mass/day.
FIG. 8A); contralateral normal brain tissue after vehicle infusion on 2 days (FIG. 8B); RG2 glioma tissue after 2 daily infusions of vehicle containing different doses of NS-1619 (50 µg NS-1619/kg body mass/day.
FIG. 8G) and normal contralateral brain tissue of the same rat (FIG. 8H)
FIG. 8I shows as a positive control the apoptotic effect of staurosporin (intracarotid injection total 20 µg/kg body mass, flow rate=0.0823 mL/min, for 15 minutes) on RG2 tumor cells implanted in Wistar rats.
FIG. 8J shows the effect on contralateral tissue. SSC-Height=size scattering height, which indicates degree of granularity or complexity of cells; FSC-Height=forward scattering height, which indicates size of the event; FL1-Height is a measure of FITC-Annexin V staining that indicates apoptotic cells; FL2-Height is a measure of propidium iodide (PI) staining that indicates necrotic cells.

Intracarotid bolus infusion of a phosphate buffered saline vehicle only (PBS, pH 7.4, 0.5% v/v ethanol), i.e., minus $K_{Ca}$ activator, on two consecutive days to rats with implanted RG2 glioma tumors, the tumor tissue contained 12% apoptotic cells and 18% necrotic (FIG. 8A). The contralateral normal brain tissue from the same rat contained a negligible number of apoptotic cells after PBS vehicle infusion (5% apoptotic cells, 2% necrotic cells; FIG. 8B). In contrast, a rat with implanted RG2 tumors that was given NS-1619 treatment (two consecutive daily doses of 50 or 100 µg NS-1619 /kg body mass). A rat receiveing 50 µg NS-1619/kg body mass had 28% apoptotic and 24% necrotic cells with the RG2 tumor (FIG. 8C) and 1% apoptotic and 1% necrotic cells in contralateral normal brain tissue (FIG. 8D). One rat receiving 100 µg NS-1619/kg body mass/day for two days had 44% apoptosis and 15% necrosis within the RG2 tumor (FIG. 8E), compared to negligible apoptosis in the normal contralateral brain tissue of the same rat (2% apoptotic cells, 5% necrotic; FIG. 8F). Another rat receiving 100 µg NS-1619/kg body mass/day for two days had 34% apoptosis and 9% necrosis within the RG2 tumor (FIG. 8G), compared to negligible apoptosis in the normal contralateral brain tissue of the same rat (2% apoptotic cells, 1% necrotic; FIG. 8H). A representative positive control, in which the known apoptotic agent staurosporin (20 µg/kg body mass) was injected as a bolus, instead of NS-1619, resulted in 35% apoptotic cells and 17% necrotic cells within the RG2 tumor tissue (FIG. 8I), compared to 5% apoptotic cells and 11% necrotic cells in normal contralateral brain tissue (FIG. 8J).

Figure 9A:
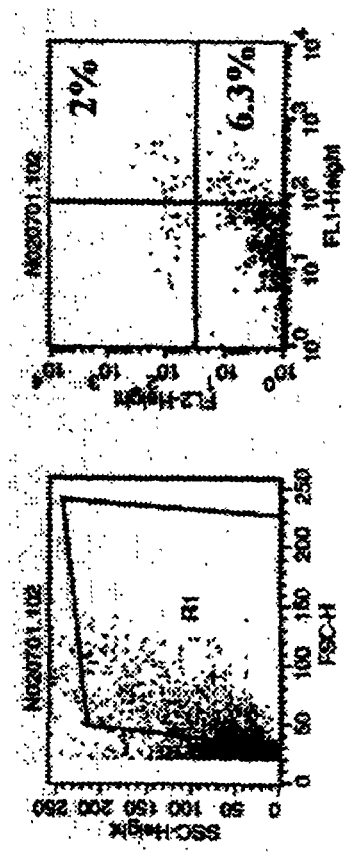
FIG. 9A); contralateral normal brain tissue after vehicle infusion on 3 days (FIG. 9B).
Figure 9B:
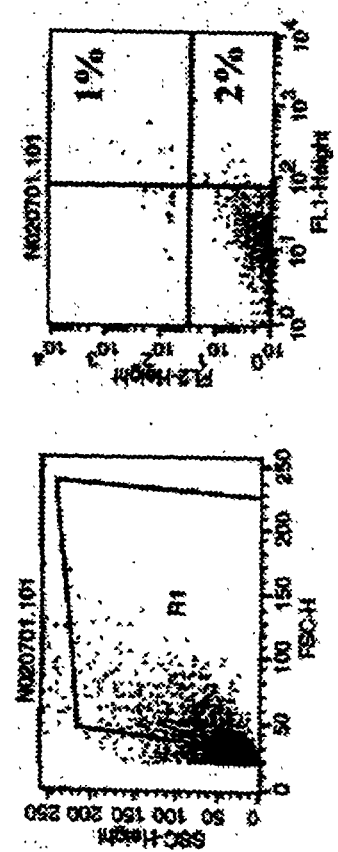
FIG. 9 illustrates the in vivo apoptosis-inducing effect, in Wistar rats having implanted RG2 tumors, of intracarotid doses of NS-1619 on three consecutive days. RG2 tumor after 3 daily infusions of vehicle ([3.2 mL PBS+1% ethanol]/kg body mass/day, flow rate=0.0823 mL/min, for 15 minutes.
FIG. 9C shows the result of three consecutive daily treatments with NS-1619 (100 µg/kg body mass/day; dose flow rate=0.0823 mL/min, for 15 minutes) in implanted RG2 glioma tumors, compared with contralateral normal brain (FIG. 9D). SSC-Height=size scattering height, which indicates degree of granularity or complexity of cells; FSC-Height=forward scattering height, which indicates size of the event; FL1-Height is a measure of FITC-Annexin V staining that indicates apoptotic cells; FL2-Height is a measure of propidium iodide (PI) staining that indicates necrotic cells.
Figure 9C:
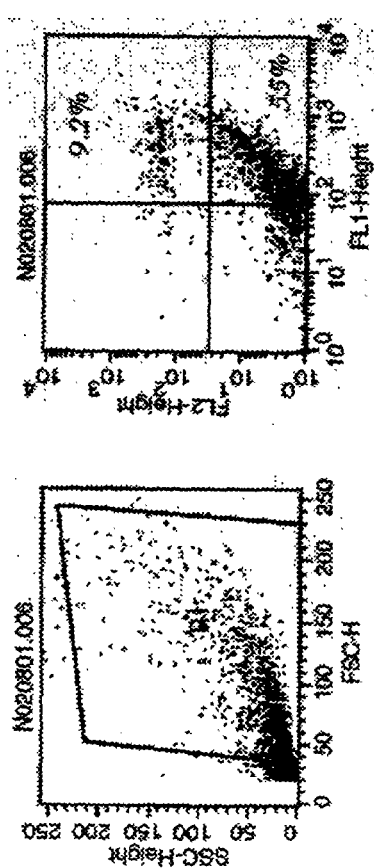
Figure 9D:
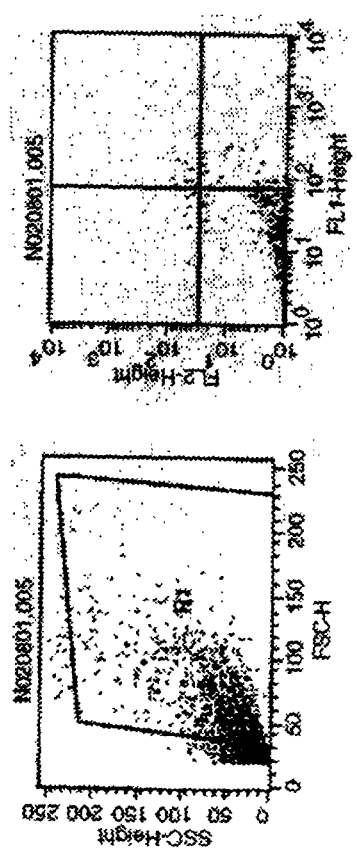

When the treatment period was extended to three consecutive days the induction of apoptosis by $K_{Ca}$ channel activator was even more pronounced. Intracarotid bolus infusion of a phosphate buffered saline vehicle only (PBS, pH 7.4, 1% v/v ethanol), i.e., minus $K_{Ca}$ channel activator, on three consecutive days to rats with implanted RG2 glioma tumors, the tumor tissue contained 6.3% apoptotic cells and 2% necrotic cells (FIG. 9A). The contralateral normal brain tissue contained a negligible number of apoptotic cells after PBS vehicle infusion (2% apoptotic cells, 1% necrotic cells; FIG. 9B). In a rat that received three consecutive daily bolus doses of NS-1619 (100 µg/kg body mass), an even higher degree of apoptosis (55%) and necrosis (9%) was detected in implanted RG2 tumor tissue (FIG. 9C), compared with contralateral normal brain (2% apoptotic and 1% necrotic cells; FIG. 9D).

Together these data also show that infusion of NS-1619 for two or three consecutive days at up to 100 µg/kg body mass didn't affect normal brain tissue considerably, while inducing a selective cell death in tumor tissue.

Figure 10:
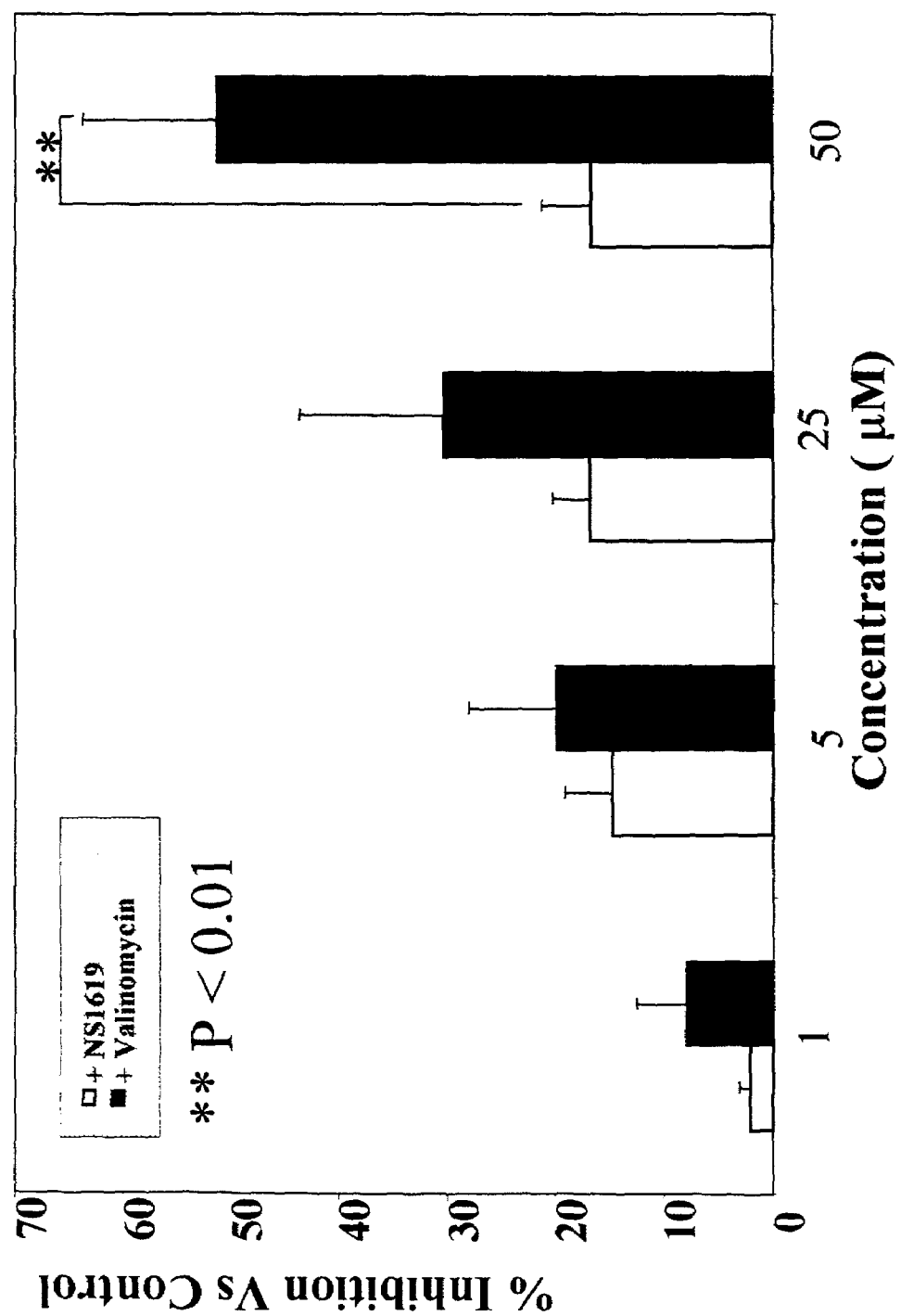
FIG. 10 shows that valinomycin (a K$^+$ ionophore) inhibited PTK activity in RG2 cell lysate in a dose-dependent manner, while NS-1619 did not significantly affect PTK activity in RG2 cell lysate. Values are mean±SD of six experiments.

Experiments showed that induction of apoptosis by the $K_{Ca}$ channel activator did not likely operate by disruption of a protein tyrosine kinase-mediated pathway. Valinomycin (a $K^+$ ionophore) inhibited PTK activity in RG2 cell lysate in a dose-dependent manner, while NS-1619 did not significantly affect PTK activity in RG2 cell lysate (FIG. 10).

Immunohistochemical Analysis Shows Potassium Channels Are More Abundant in Neovasculature and Malignant Cells Compared to Normal Tissue.

Figure 11A:
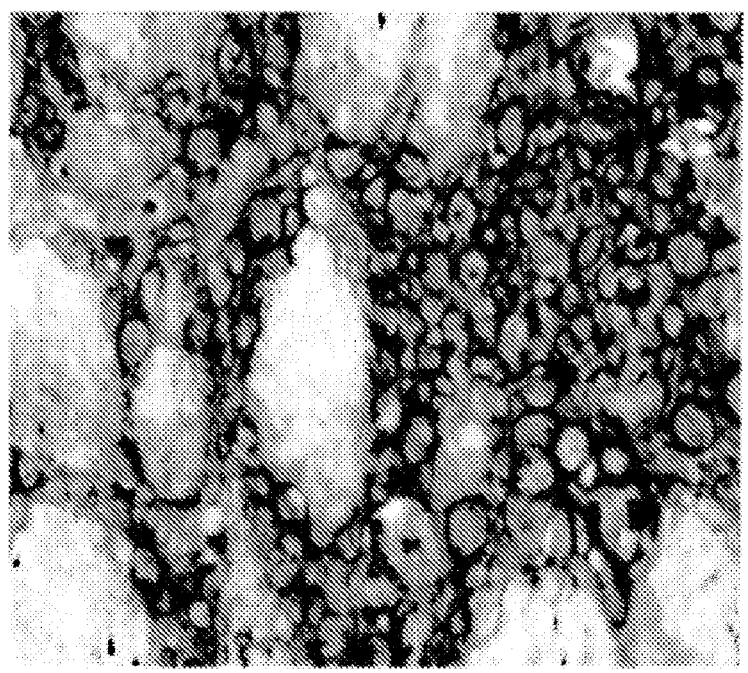
FIG. 11 shows intense over-expression of $K_{Ca}$ as indicated by anti-$K_{Ca}$ immunostain of rat glioma tissue (FIG. 11B), compared to normal contralateral brain tissue (FIG. 11A). Magnification is 100×.
Figure 11B:
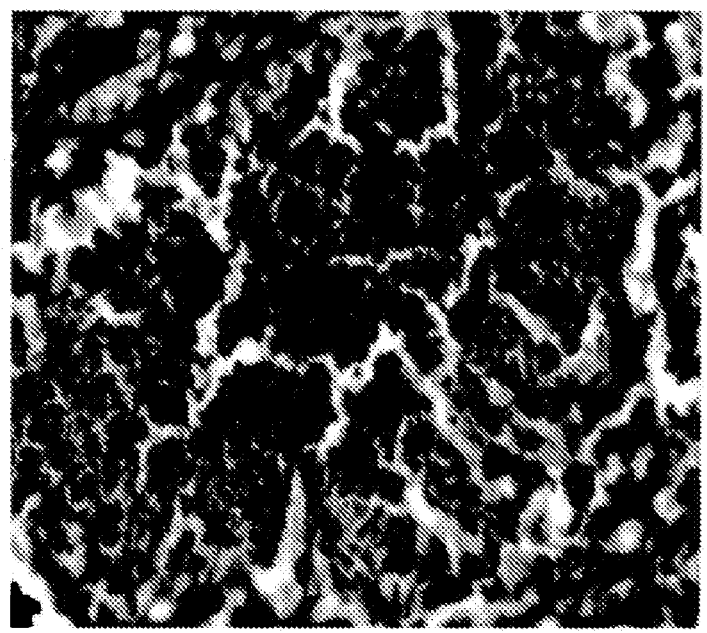

$K_{Ca}$ channel protein was immunolocalized using a specific antibody as described above. Immunohistochemical analysis showed that $K_{Ca}$ channels were more highly localized in tumor tissue in RG2 bearing rat brain sections (FIG. 11B), compared to sections of normal contralateral tissue (FIG. 11A). These immunohistochemical results are consistent with results showing activation of $K_{Ca}$ channels by NS-1619 selectively induced apoptosis in malignant cells compared to normal cells.

Together, the apoptosis and immunohistochemical data demonstrate that compounds that activate calcium dependent potassium channels can be used to selectively induce apoptosis of malignant cells in malignant tumor tissue.

The foregoing examples being illustrative but not an exhaustive description of the embodiments of the present invention, the following claims are presented.

We claim:

1. A method of inhibiting the growth of a malignant tumor in a mammalian subject, comprising:

providing a calcium-activated potassium channel activator; and administering to a mammalian subject having a malignant tumor that comprises a malignant cell, the calcium-activated potassium channel activator under conditions and in an amount sufficient to induce apoptosis of the cell, whereby growth of the malignant tumor is inhibited, and wherein the malignant cell is a glioma or astrocytoma cell and the calcium-activated potassium channel activator is 1,3-dihydro-1-[2-hydroxy-5-(trifluoromethyl)phenyl]-5-(trifluoromethyl)-2H-benzimidazole-2-one, and wherein the calcium-activated potassium channel activator is administered to the mammalian subject at a dose rate of about 0.075 to about 150 µg kg$^{-1}$ min$^{-1}$.

2. The method of claim 1, wherein the malignant tumor is a glioma, a glioblastoma, an oligodendroglioma, an astrocytoma, an ependymoma, a primitive neuroectodermal tumor or a neuroblastoma.

3. The method of claim 1, wherein the malignant tumor is contained in the skull, brain, spine, thorax, lung, abdomen, peritoneum, prostate, ovary, uterus, breast, stomach, liver, bowel, colon, rectum, bone, lymphatic system, or skin, of said subject.

4. The method of claim 1, wherein said mammalian subject is a human, a non-human primate, a canine, a feline, a bovine, a porcine, an ovine, a mouse, a rat, a gerbil, a hamster, or a rabbit.

5. The method of claim 1, wherein administering the calcium-activated potassium channel activator is by intravenous or intra-arterial injection.

6. The method of claim 1, wherein the tumor is an intracranial tumor and the calcium-activated potassium channel activator is administered by intracarotid infusion.

7. The method of claim 1, wherein the calcium-activated potassium channel activator is administered to the mammalian subject by a bolus injection.

8. The method of claim 1, wherein the calcium-activated potassium channel activator is administered to the mammalian subject in an amount from about 0.075 to 1500 micrograms per kilogram body mass.

9. The method of claim 1, wherein the calcium-activated potassium channel activator is administered to the subject in an amount from about 0.075 to 150 micrograms per kilogram body mass.

10. The method of claim 1, wherein the calcium-activated potassium channel activator is administered to the mammalian subject at a dose rate of about 0.075 to about 15 µg kg$^{-1}$ min$^{-1}$.

11. A method of inhibiting the growth of a glial tumor in a mammalian subject, comprising:

providing a calcium-activated potassium channel activator; and administering to a mammalian subject having a glial tumor that comprises a malignant cell, the calcium-activated potassium channel activator under conditions and in an amount sufficient to induce apoptosis of the cell, whereby growth of the malignant tumor is inhibited, and wherein the malignant cell is a glioma or astrocytoma cell and the calcium-activated potassium channel activator is 1,3-dihydro-1-[2-hydroxy-5-(trifluoromethyl)phenyl]-5-(trifluoromethyl)-2H-benzimidazole-2-one, and wherein the calcium-activated potassium channel activator is administered to the mammalian subject at a dose rate of about 0.075 to about 150 µg kg$^{-1}$ min$^{-1}$.

12. The method of claim 11, wherein said mammalian subject is a human, a non-human primate, a canine, a feline, a bovine, a porcine, an ovine, a mouse, a rat, a gerbil, a hamster, or a rabbit.

13. The method of claim 11, wherein administering the calcium-activated potassium channel activator is by intravenous or intra-arterial injection.

14. The method of claim 11, wherein the tumor is an intracranial tumor and the calcium-activated potassium channel activator is administered by intracarotid infusion.

15. The method of claim 11, wherein the calcium-activated potassium channel activator is administered to the mammalian subject by a bolus injection.

16. The method of claim 11, wherein the calcium-activated potassium channel activator is administered to the mammalian subject in an amount from about 0.075 to 1500 micrograms per kilogram body mass.

17. The method of claim 11, wherein the calcium-activated potassium channel activator is administered to the subject in an amount from about 0.075 to 150 micrograms per kilogram body mass.

18. The method of claim 11, wherein the calcium-activated potassium channel activator is administered to the mammalian subject at a dose rate of about 0.075 to about 15 µg kg$^{-1}$ min$^{-1}$.

* * * * *

UNITED STATES PATENT AND TRADEMARK OFFICE
CERTIFICATE OF CORRECTION

| | |
|---|---|
| PATENT NO. | : 7,211,561 B2 |
| APPLICATION NO. | : 09/976961 |
| DATED | : May 1, 2007 |
| INVENTOR(S) | : Keith L. Black et al. |

It is certified that error appears in the above-identified patent and that said Letters Patent is hereby corrected as shown below:

In column 1, after the cross-reference to related applications but before the "Field of the Invention" section, insert the following:

--FEDERAL SUPPORT
The U.S. Government has a paid-up license in this invention and the right in limited circumstances to require the patent owner to license others on reasonable terms as provided for by the terms of Grant No. N532103 awarded by the National Institutes of Health.--

Signed and Sealed this
Twelfth Day of February, 2013

Teresa Stanek Rea
*Acting Director of the United States Patent and Trademark Office*